United States Patent
Hillis et al.

(10) Patent No.: US 9,459,470 B2
(45) Date of Patent: Oct. 4, 2016

(54) VISION MODIFICATION WITH REFLECTED IMAGE

(71) Applicant: Searete LLC, Bellevue, WA (US)

(72) Inventors: W. Daniel Hillis, Cambridge, MA (US); Roderick A. Hyde, Redmond, WA (US); Muriel Y. Ishikawa, Livermore, CA (US); Edward K. Y. Jung, Bellevue, WA (US); Nathan P. Myhrvold, Medina, WA (US); Clarence T. Tegreene, Mercer Island, WA (US); Lowell L. Wood, Jr., Bellevue, WA (US)

(73) Assignee: Gearbox, LLC, Bellevue, WA (US)

( * ) Notice: Subject to any disclaimer, the term of this patent is extended or adjusted under 35 U.S.C. 154(b) by 0 days.

(21) Appl. No.: 14/879,194

(22) Filed: Oct. 9, 2015

(65) Prior Publication Data

US 2016/0085089 A1    Mar. 24, 2016

Related U.S. Application Data

(60) Continuation of application No. 13/385,889, filed on Mar. 12, 2012, now Pat. No. 9,155,483, which is a continuation-in-part of application No. 12/590,439, filed on Nov. 6, 2009, now Pat. No. 8,282,212, which (Continued)

(51) Int. Cl.
*A61F 2/16* (2006.01)
*G02C 7/08* (2006.01)
(Continued)

(52) U.S. Cl.
CPC ............ *G02C 7/081* (2013.01); *A61B 3/0025* (2013.01); *A61B 3/14* (2013.01); *A61B 5/04001* (2013.01); *A61F 2/1624* (2013.01); *G02C 3/02* (2013.01);

(Continued)

(58) Field of Classification Search
CPC .... A61F 2/147; A61F 2/1613; A61F 2/1635; A61B 3/103; A61B 3/1015; G02C 7/04; G02C 7/08
USPC ......... 351/159.01–159.03, 159.73, 200, 205, 351/246; 623/6.11, 6.22
See application file for complete search history.

(56) References Cited

U.S. PATENT DOCUMENTS 3,161,718 A   12/1964  DeLuca
3,245,315 A    4/1966  Marks et al.
(Continued)

FOREIGN PATENT DOCUMENTS

KR     2003/020033 A     3/2003
WO   WO 02/097511 A1   12/2002

OTHER PUBLICATIONS

Carandini, Matteo; Heeger, David J.; Senn, Walter; "A Synaptic Explanation of Suppression in Visual Cortex"; The Journal of Neuroscience; bearing a date of Nov. 15, 2002; vol. 22.; pp. 10053-10065.

(Continued)

*Primary Examiner* — James Greece

(57) ABSTRACT

Various embodiments of methods and systems for improving and enhancing vision are disclosed. Adjustable lenses or optical systems may be used to provide adaptive vision modification. In some embodiments, vision modification may be responsive to the current state of the user's visual system. Certain embodiments provide correction of the subject's near and far vision. Other embodiments provide enhancement of vision beyond the physiological ranges of focal length or magnification.

43 Claims, 15 Drawing Sheets

Related U.S. Application Data is a division of application No. 11/495,165, filed on Jul. 27, 2006, now Pat. No. 8,104,892, which is a continuation-in-part of application No. 11/004,473, filed on Dec. 3, 2004, now Pat. No. 7,350,919, which is a continuation-in-part of application No. 11/004,713, filed on Dec. 3, 2004, now Pat. No. 7,334,894, which is a continuation-in-part of application No. 11/004,533, filed on Dec. 3, 2004, now Pat. No. 7,334,892, which is a continuation-in-part of application No. 11/004,731, filed on Dec. 3, 2004, now Pat. No. 7,486,988, which is a continuation-in-part of application No. 11/004,551, filed on Dec. 3, 2004, now Pat. No. 7,344,244, said application No. 13/385,889 is a continuation-in-part of application No. 11/495,167, filed on Jul. 27, 2006, now Pat. No. 7,656,569, which is a continuation-in-part of application No. 11/004,473, said application No. 13/385,889 is a continuation-in-part of application No. 12/321,560, filed on Jan. 21, 2009, now Pat. No. 7,931,373, which is a division of application No. 11/495,167, which is a continuation-in-part of application No. 11/004,473, said application No. 13/385,889 is a continuation-in-part of application No. 11/523,172, filed on Sep. 18, 2006, now Pat. No. 8,244,342, which is a division of application No. 11/004,731, said application No. 13/385,889 is a continuation-in-part of application No. 12/072,883, filed on Feb. 27, 2008, now Pat. No. 8,562,540, which is a division of application No. 11/004,731, said application No. 13/385,889 is a continuation-in-part of application No. 12/590,402, filed on Nov. 6, 2009, now Pat. No. 8,109,632.

(51) Int. Cl.
   *A61B 5/04*   (2006.01)
   *A61B 3/00*   (2006.01)
   *A61B 3/14*   (2006.01)
   *G02C 3/02*   (2006.01)
   *G02C 7/04*   (2006.01)
   *G02C 7/10*   (2006.01)
   *G02C 11/00*  (2006.01)

(52) U.S. Cl.
   CPC ............... *G02C 7/04* (2013.01); *G02C 7/085* (2013.01); *G02C 7/101* (2013.01); *G02C 11/10* (2013.01)

(56) References Cited

U.S. PATENT DOCUMENTS

| | | |
|---|---|---|
| 3,507,988 A | 4/1970 | Holmes |
| 3,614,215 A | 10/1971 | Mackta |
| 3,738,734 A | 6/1973 | Tait et al. |
| 3,819,256 A | 6/1974 | Bellows et al. |
| 4,168,882 A | 9/1979 | Hopkins |
| 4,174,156 A | 11/1979 | Glorieux |
| 4,181,408 A | 1/1980 | Senders |
| 4,190,330 A | 2/1980 | Berreman |
| 4,255,023 A | 3/1981 | House |
| 4,261,655 A | 4/1981 | Honigsbaum |
| 4,264,154 A | 4/1981 | Petersen |
| 4,279,474 A | 7/1981 | Belgorod |
| 4,300,818 A | 11/1981 | Schachar |
| 4,373,218 A | 2/1983 | Schachar |
| 4,395,736 A | 7/1983 | Fraleux |
| 4,403,840 A | 9/1983 | Okun |
| 4,418,990 A | 12/1983 | Gerber |
| 4,429,959 A | 2/1984 | Walters |
| 4,444,471 A | 4/1984 | Ford, Jr. et al. |
| 4,466,705 A | 8/1984 | Michelson |
| 4,466,706 A | 8/1984 | Lamothe, II |
| 4,500,180 A | 2/1985 | Stevens |
| 4,564,267 A | 1/1986 | Nishimoto |
| 4,572,616 A | 2/1986 | Kowel et al. |
| 4,601,545 A | 7/1986 | Kern |
| 4,609,824 A | 9/1986 | Munier et al. |
| 4,697,598 A | 10/1987 | Bernard et al. |
| 4,709,996 A | 12/1987 | Michelson |
| 4,756,605 A | 7/1988 | Okada et al. |
| 4,772,094 A | 9/1988 | Sheiman |
| 4,787,903 A | 11/1988 | Grendahl |
| 4,795,248 A | 1/1989 | Okada et al. |
| 4,818,095 A | 4/1989 | Takeuchi |
| 4,836,652 A | 6/1989 | Oishi et al. |
| 4,842,601 A | 6/1989 | Smith |
| 4,844,086 A | 7/1989 | Duffy |
| 4,904,063 A | 2/1990 | Okada et al. |
| 4,907,860 A | 3/1990 | Noble |
| 4,919,520 A | 4/1990 | Okada et al. |
| 4,927,241 A | 5/1990 | Kuijk |
| 4,945,242 A | 7/1990 | Berger et al. |
| 4,952,788 A | 8/1990 | Berger et al. |
| 4,953,968 A | 9/1990 | Sherwin et al. |
| 4,955,389 A | 9/1990 | Schneider |
| 4,961,639 A | 10/1990 | Lazarus |
| 4,968,127 A | 11/1990 | Russell et al. |
| 4,974,602 A | 12/1990 | Abraham-Fuchs et al. |
| 4,981,342 A | 1/1991 | Fiala |
| 4,991,951 A | 2/1991 | Mizuno et al. |
| 5,015,086 A | 5/1991 | Okaue et al. |
| 5,020,538 A | 6/1991 | Morgan et al. |
| 5,052,401 A | 10/1991 | Sherwin |
| 5,066,301 A | 11/1991 | Wiley |
| 5,073,021 A | 12/1991 | Marron |
| 5,076,665 A | 12/1991 | Petersen |
| 5,091,801 A | 2/1992 | Ebstein |
| 5,108,169 A | 4/1992 | Mandell |
| 5,108,429 A | 4/1992 | Wiley |
| 5,142,411 A | 8/1992 | Fiala |
| 5,171,266 A | 12/1992 | Wiley et al. |
| 5,182,585 A | 1/1993 | Stoner |
| 5,184,156 A | 2/1993 | Black et al. |
| 5,187,672 A | 2/1993 | Chance et al. |
| 5,203,788 A | 4/1993 | Wiley |
| 5,208,688 A | 5/1993 | Fergason et al. |
| 5,229,885 A | 7/1993 | Quaglia |
| 5,239,412 A | 8/1993 | Naka et al. |
| 5,306,926 A | 4/1994 | Yonemoto |
| 5,309,095 A | 5/1994 | Ahonen et al. |
| 5,323,777 A | 6/1994 | Ahonen et al. |
| 5,324,930 A | 6/1994 | Jech, Jr. |
| 5,329,322 A | 7/1994 | Yancey |
| 5,351,100 A | 9/1994 | Schwenzfeier et al. |
| 5,352,886 A | 10/1994 | Kane |
| 5,359,444 A | 10/1994 | Piosenka et al. |
| 5,382,986 A | 1/1995 | Black et al. |
| 5,440,357 A | 8/1995 | Quaglia |
| 5,443,506 A | 8/1995 | Garabet |
| 5,451,766 A | 9/1995 | Van Berkel |
| 5,488,439 A | 1/1996 | Weltmann |
| 5,491,583 A | 2/1996 | Robb |
| 5,526,067 A | 6/1996 | Cronin et al. |
| 5,627,674 A | 5/1997 | Robb |
| 5,629,747 A | 5/1997 | Miyake |
| 5,629,790 A | 5/1997 | Neukermans et al. |
| 5,644,374 A | 7/1997 | Mukaiyama et al. |
| 5,654,786 A | 8/1997 | Bylander |
| 5,655,534 A | 8/1997 | Ilmoniemi |
| 5,684,637 A | 11/1997 | Floyd |
| 5,687,291 A | 11/1997 | Smyth |
| 5,712,721 A | 1/1998 | Large |
| 5,728,155 A | 3/1998 | Anello et al. |
| 5,739,959 A | 4/1998 | Quaglia |
| 5,748,382 A | 5/1998 | Maguire, Jr. |
| 5,777,719 A | 7/1998 | Williams et al. |
| 5,792,051 A | 8/1998 | Chance |

(56) References Cited

U.S. PATENT DOCUMENTS

| | | | |
|---|---|---|---|
| 5,815,233 A | 9/1998 | Morokawa et al. | |
| 5,840,040 A | 11/1998 | Altschuler et al. | |
| 5,853,370 A | 12/1998 | Chance et al. | |
| 5,861,936 A | 1/1999 | Sorensen | |
| 5,900,720 A | 5/1999 | Kallman et al. | |
| 5,949,521 A | 9/1999 | Williams et al. | |
| 5,956,183 A | 9/1999 | Epstein et al. | |
| 5,973,852 A | 10/1999 | Task | |
| 5,980,037 A | 11/1999 | Conway | |
| 5,995,857 A | 11/1999 | Toomim et al. | |
| 6,013,101 A | 1/2000 | Israel | |
| 6,014,582 A | 1/2000 | He | |
| 6,033,073 A | 3/2000 | Potapova et al. | |
| 6,066,084 A | 5/2000 | Edrich et al. | |
| 6,069,742 A | 5/2000 | Silver | |
| 6,120,538 A | 9/2000 | Rizzo, III et al. | |
| 6,177,800 B1 | 1/2001 | Kubby et al. | |
| 6,195,576 B1 | 2/2001 | John | |
| 6,199,986 B1* | 3/2001 | Williams et al. | 351/221 |
| 6,212,015 B1 | 4/2001 | Heimer | |
| 6,227,667 B1 | 5/2001 | Halldorsson et al. | |
| 6,233,480 B1 | 5/2001 | Hochman et al. | |
| 6,256,531 B1 | 7/2001 | Ilmoniemi et al. | |
| 6,288,846 B1 | 9/2001 | Stoner, Jr. | |
| 6,318,857 B1 | 11/2001 | Shirayanagi | |
| 6,325,508 B1 | 12/2001 | Decreton et al. | |
| 6,352,345 B1 | 3/2002 | Zolten | |
| 6,369,954 B1 | 4/2002 | Berge et al. | |
| 6,370,414 B1 | 4/2002 | Robinson | |
| 6,379,989 B1 | 4/2002 | Kubby et al. | |
| 6,394,602 B1 | 5/2002 | Morrison et al. | |
| 6,397,099 B1 | 5/2002 | Chance | |
| 6,399,405 B1 | 6/2002 | Chen et al. | |
| 6,445,509 B1 | 9/2002 | Alden | |
| 6,491,394 B1 | 12/2002 | Blum et al. | |
| 6,517,203 B1 | 2/2003 | Blum et al. | |
| 6,523,954 B1 | 2/2003 | Kennedy et al. | |
| 6,523,955 B1 | 2/2003 | Eberl et al. | |
| 6,530,816 B1 | 3/2003 | Chiu | |
| 6,542,309 B2 | 4/2003 | Guy | |
| 6,544,170 B1 | 4/2003 | Kajihara et al. | |
| 6,580,858 B2 | 6/2003 | Chen et al. | |
| 6,615,074 B2 | 9/2003 | Mickle et al. | |
| 6,619,799 B1 | 9/2003 | Blum et al. | |
| 6,638,304 B2 | 10/2003 | Azar | |
| 6,647,296 B2 | 11/2003 | Fischell et al. | |
| 6,655,035 B2 | 12/2003 | Ghandi et al. | |
| 6,658,179 B2 | 12/2003 | Kubby et al. | |
| 6,690,959 B2 | 2/2004 | Thompson | |
| 6,694,180 B1 | 2/2004 | Boesen | |
| 6,697,660 B1 | 2/2004 | Robinson | |
| 6,709,108 B2 | 3/2004 | Levine et al. | |
| 6,715,876 B2 | 4/2004 | Floyd | |
| 6,733,130 B2 | 5/2004 | Blum et al. | |
| 6,744,550 B2 | 6/2004 | Neukermans et al. | |
| 6,747,806 B2 | 6/2004 | Gelbart | |
| 6,752,499 B2 | 6/2004 | Aller | |
| 6,762,867 B2 | 7/2004 | Lippert et al. | |
| 6,768,246 B2 | 7/2004 | Pelrine et al. | |
| 6,801,719 B1 | 10/2004 | Szajewski et al. | |
| 7,041,133 B1 | 5/2006 | Azar | |
| 7,141,065 B2 | 11/2006 | Azar | |
| 7,261,736 B1 | 8/2007 | Azar | |
| 7,334,894 B2 | 2/2008 | Hillis et al. | |
| 7,350,919 B2 | 4/2008 | Hillis et al. | |
| 7,457,434 B2 | 11/2008 | Azar | |
| 7,470,027 B2 | 12/2008 | Hillis et al. | |
| 7,594,727 B2 | 9/2009 | Hillis et al. | |
| 8,043,370 B2 | 10/2011 | Bretthauer et al. | |
| 8,216,309 B2 | 7/2012 | Azar | |
| 9,254,189 B2 | 2/2016 | Azar | |
| 2002/0036750 A1 | 3/2002 | Eberl et al. | |
| 2002/0140899 A1* | 10/2002 | Blum et al. | 351/159 |
| 2002/0140902 A1 | 10/2002 | Guirao et al. | |
| 2003/0014091 A1 | 1/2003 | Rastegar et al. | |
| 2003/0018383 A1 | 1/2003 | Azar | |
| 2003/0058406 A1 | 3/2003 | Blum et al. | |
| 2003/0158587 A1 | 8/2003 | Esteller et al. | |
| 2003/0164923 A1 | 9/2003 | Hirohara et al. | |
| 2003/0165648 A1 | 9/2003 | Lobovsky et al. | |
| 2003/0231293 A1 | 12/2003 | Blum et al. | |
| 2004/0051846 A1 | 3/2004 | Blum et al. | |
| 2004/0056986 A1 | 3/2004 | Blum et al. | |
| 2005/0036109 A1 | 2/2005 | Blum et al. | |
| 2006/0012747 A1 | 1/2006 | Wahl et al. | |
| 2006/0028734 A1 | 2/2006 | Kuiper et al. | |
| 2006/0095128 A1 | 5/2006 | Blum et al. | |
| 2006/0206205 A1 | 9/2006 | Azar | |
| 2006/0238701 A1 | 10/2006 | Blum | |
| 2007/0019279 A1 | 1/2007 | Goodall et al. | |
| 2007/0028931 A1 | 2/2007 | Hillis et al. | |
| 2007/0260307 A1 | 11/2007 | Azar | |
| 2009/0105817 A1 | 4/2009 | Bretthauer et al. | |
| 2009/0326652 A1 | 12/2009 | Azar | |
| 2012/0236257 A1 | 9/2012 | Hillis et al. | |
| 2012/0239144 A1 | 9/2012 | Azar | |
| 2013/0073038 A1 | 3/2013 | Azar | |
| 2015/0057748 A1 | 2/2015 | Azar | |

OTHER PUBLICATIONS

Center for Adaptive Opitcs: "How Does an Adaptive Optics System Work?"; bearing a date of 2002; pp. 1-2., located at : http://www.cfao.ucolick.org/ao/how.php , printed on Jul. 14, 2004.

Center for Adaptive Optics: "Other AO Primers"; bearing a date of 2002; pp. 1, located at http://www.cfaco.ucolick.org/ao/other.php , printed on Jul. 14, 2004.

Chance, Britton; Nioka, Shoko; Chen, Yu; "Shining New Light on Brain Function"; Spie's oemagazine; bearing a date of Jul. 2003; pp. 16-19 with 1 sheet of figures.

Croft, Mary Ann; Kaufman, Paul L.; Crawford, Kathryn S.; Neider, Michael W.; Glasser, Adrian; Bito, Laszlo Z.; "Accommodation dynamics in aging rhesus monkeys"; bearing a date of 1998; pp. 1885-1897.

Fantini, Sergio; Franceschini, Maria Angela; Gratton, Enrico; Hueber, Dennis; Rosenfeld, Warren; Maulik, Dev; Stubblefield, Phillip G.; Stankovic, Miljan R.; "Non-invasive optical mapping of the piglet brain in real time"; Optics Express; bearing dates of: Mar. 9, 1999; Apr. 7, 1999; Apr. 12, 1999; vol. 4, No. 8; pp. 308-314.

Fantini, Sergio; Heffer, Erica L.; Franceschini, Maria Angela; Gotz, Linda; Heinig, Anke; Heywang-Kobrunner, Sylvia; Schutz, Oliver; Siebold, Horst; "Optical Mammography with Intensity-Modulated Light"; pp. 1-7; printed on Aug. 30, 2004.

Firelily Designs; "Color Vision, Color Deficiency"; pp. 1-12; located at http://firelily.com/opinions/color.html; printed on Dec. 13, 2004; bearing a Copyright date of 1996-2003.

FVM: Program Abstracts; "Program Abstracts"; pp. 1-25; located at http://www.cvs.rochester.edu/fvm_progabst.html; printed on Dec. 13, 2004.

Gratton, Gabriele; Fabiani, Monica; Corballis, Paul M.; Hood, Donald C.; Goodman-Wood, Marsha R.; Hirsch, Joy; Kim, Karl; Friedman, David; Gratton, Enrico; "Fast and Localized Event-Related Optical Signals (EROS) in the Human Occipital Cortex: Comparisons with the Visual Evoked Potential and fMRI"; Neuroimage 6; bearing a date of 1997 and Dec. 24, 1996; pp. 168-180 ; Article No. NI970298.

Heeger, David J.; "Linking visual perception with human brain activity"; Current Opionion in Neurobiology; bearing a date of 1999, 9; pp. 474-479; located at: http://biomednet.com/elecref/0959438800900474.

Heeger, David; "Recent Publications"; printed on Sep. 30, 2004; pp. 1-20; located at: http://www.cns.nyu.edu/~david/publications.html.

Heeger, David J.; Ress, David; "What Does fMRI Tell Us About Neuronal Activity?"; Feb. 2002; vol. 3; pp. 142-151; located at: www.nature.com/reviews/neuro.

Intes, X.; Chance, B.; Holboke, M.J.; Yodh, A.G.; "Interfering diffusive photon-density waves with an absorbing-flourescent inhomogeneity"; Optics Express; bearing dates of Nov. 9, 2000, Jan. 17, 2001 and Jan. 29, 2001; vol. 8, No. 3; pp. 223-231.

(56) References Cited

OTHER PUBLICATIONS

Intes, X.; Ntziachristos, V.; Chance B.; "Analytical model for dual-interfering sources diffuse optical tomography"; Optics Express; bearing dates of Sep. 19, 2001, Dec. 14, 2001 and Jan. 14, 2002; vol. 10, No. 1; pp. 2-14.

Krulevitch, Peter; Bierden, Paul; Bifano, Thomas; Carr, Emily; Diams, Clara; Dyson, Harold; Helmbrecht, Michael; Kurczynski, Peter; Muller, Richard; Olivier, Scot; Peter, Yves-Alain; Sadoulet, Bernard; Solgaard, Olav; and Yang, E.H.; "MOEMS spatial light modulator development at the Center for Adaptive Optics"; bearing a date of 2003; pp. 227-234.

Lewotsky, Kristin; "Seeing into the Body"; Spie's OEMagazine; bearing a date of Jul. 2003; p. 15.

Makeig, Scott; Westerfield, Marissa; Townsend, Jeanne; Jung, Tzyy-Ping; Courchesne, Eric; Sejnowski,Terrence J.; "Functionally Independent Componenets of Early Event-Related Potentials in a Visual Spatial Attention Task"; Philosophical Transactions of the Royal Society; Biological Sciences: 354: 1135-44; bearing a date of Jun. 5, 1999; pp. 1-23.

Malonek, Dov; Dirnagl, Ulrich; Lindauer, Ute; Yamada, Katsuya; Kanno, Iwao; Grinvald, Amiram; "Vascular imprints of neuronal activity: Relationships between the dynamics of cortical blood flow, oxygenation, and volume changes following sensory stimulation"; Proc. Natl. Acad. Sci. USA, Neurobiology; bearing dates of Oct. 24, 1997; Jun. 9, 1997; and Dec. 1997; vol. 94; pp. 14826-14831.

Morgan, S.P.; Yong, K.Y.; "Controlling the phase response of a diffusive wave phased array system"; Optics Express; bearing dates of Oct. 19, 2000, Dec. 7, 2000, and Dec. 18, 2000; Vo. 7, No. 13; pp. 540-546.

Neri, Peter; Heeger, David J.; "Spatiotemporal mechanisms for detecting and identifying image features in human vision"; Nature Neuroscience; bearing dates of Jul. 8, 2002 and Aug. 2002; vol. 5, No. 8; pp. 812-816.

Photonics at Imperial College; Applied Optics: "Wavefront sensing of the human eye"; "The double-pass process"; printed on Jul. 14, 2004; pp. 1; located at: http://op.ph.ic.ac.uk/research/index.html.

Photonics at Imperial College; Applied Optics: "Wavefront sensing of the human eye"; "Single-pass measurement of the wave aberration of the human eye"; bearing a date of Jul. 14, 2004; pp. 1-2; printed on Jul. 14, 2004; located at: http://op.ph.ic.ac.uk/research/index.html.

R&D Where Innovation Begins; editorial: "Vision Correction for the $21^{st}$ Century"; printed on Aug. 30, 2004; pp. 1-3; located at: http://www.rdmag.com/Scripts/ShowPR.asp?PUBCODE=014&ACCT=1400000100&ISSUE=0401&RELTYPE=PR&PROCODE=00000000&PRODLETT=K.

Ress, David; Heeger, David J.; "Neuronal correlates of perception in early visual cortex"; Nature Neuroscience; bearing dates of Mar. 10, 2003 and Apr. 2003; vol. 6., No. 4; pp. 414-420.

Schaeffel, F ; Wilhelm, H.; Zrenner, E.; "Inter-individual variability in the dynamics of natural accommodation in humans: relation to age and refractive errors"; The Journal of Physiology; bearing a date of 1993; pp. 1-3; Copyright 1993 by The Physiological Society:; printed on Jul. 13, 2004; located at: http://jp.physoc.org/cgi/content/abstract/461/1/301.

Starner, T; "Human-powered wearable computing"; Systems Journal; IBM Corporation; bearing various dates of 1996 and 1998; pp. 1-14; printed on Jun. 1, 2004; located at: http://www.research.ibm.com/journal/sj/mit/sectione/starner.html.

\* cited by examiner

VISION MODIFICATION WITH REFLECTED IMAGE

CROSS-REFERENCE TO RELATED APPLICATIONS

The present application is related to, claims the earliest available effective filing date(s) from (e.g., claims earliest available priority dates for other than provisional patent applications; claims benefits under 35 USC §119(e) for provisional patent applications), and incorporates by reference in its entirety all subject matter of the following listed application(s); the present application also claims the earliest available effective filing date(s) from, and also incorporates by reference in its entirety all subject matter of any and all sibling, parent, grandparent, great-grandparent, etc. applications of the following listed application(s):

For purposes of the USPTO extra-statutory requirements, the present application constitutes a continuation of U.S. patent application Ser. No. 13/385,889, entitled VISION MODIFICATION WITH REFLECTED IMAGE, naming W. Daniel Hillis, Roderick A. Hyde, Muriel Y. Ishikawa, Edward K. Y. Jung, Nathan P. Myhrvold, Clarence T. Tegreene, and Lowell L. Wood, Jr. as inventors, filed 12 Mar. 2012, which is currently co-pending or is an application of which a currently co-pending application is entitled to the benefit of the filing date, which is a continuation-in-part of U.S. patent application Ser. No. 12/590,439, entitled VISION MODIFICATION WITH REFLECTED IMAGE, naming W. Daniel Hillis, Roderick A. Hyde, Muriel Y. Ishikawa, Edward K. Y. Jung, Nathan P. Myhrvold, Clarence T. Tegreene, and Lowell L. Wood, Jr. as inventors, filed 6 Nov. 2009, now U.S. Pat. No. 8,282,212, which is a divisional of U.S. patent application Ser. No. 11/495,165, entitled VISION MODIFICATION WITH REFLECTED IMAGE, naming W. Daniel Hills, Roderick A. Hyde, Muriel Y. Ishikawa, Edward K. Y. Jung, Nathan P. Myhrvold, Clarence T. Tegreene, and Lowell L. Wood, Jr. as inventors, filed 27 Jul. 2006, now U.S. Pat. No. 8,104,892, which is a continuation-in-part of U.S. patent application Ser. No. 11/004,473, entitled VISION MODIFICATION WITH REFLECTED IMAGE, naming W. Daniel Hillis, Roderick A. Hyde, Muriel Y. Ishikawa, Edward K. Y. Jung, Nathan P. Myhrvold, Clarence T. Tegreene, and Lowell L. Wood, Jr. as inventors, filed 3 Dec. 2004, now U.S. Pat. No. 7,350,919, which is a continuation-in-part of U.S. patent application Ser. No. 11/004,713, entitled TEMPORAL VISION MODIFICATION, naming W. Daniel Hillis, Roderick A. Hyde, Muriel Y. Ishikawa, Edward K. Y. Jung, Nathan P. Myhrvold, Clarence T. Tegreene, and Lowell L. Wood, Jr. as inventors, filed 3 Dec. 2004, now U.S. Pat. No. 7,334,894, which is a continuation-in-part of U.S. patent application Ser. No. 11/004,533, entitled METHOD AND SYSTEM FOR VISION ENHANCEMENT, naming Eleanor V. Goodall, W. Daniel Hillis, Roderick A. Hyde, Muriel Y. Ishikawa, Edward K. Y. Jung, Nathan P. Myhrvold, and Lowell L. Wood, Jr. as inventors, filed 3 Dec. 2004, now U.S. Pat. No. 7,334,892, which is a continuation-in-part of U.S. patent application Ser. No. 11/004,731, entitled METHOD AND SYSTEM FOR ADAPTIVE VISION MODIFICATION, naming Eleanor V. Goodall, W. Daniel Hillis, Roderick A. Hyde, Muriel Y. Ishikawa, Edward K. Y. Jung, Nathan P. Myhrvold, and Lowell L. Wood, Jr. as inventors, filed 3 Dec. 2004, now U.S. Pat. No. 7,486,988, which is a continuation-in-part of U.S. patent application Ser. No. 11/004,551, entitled ADJUSTABLE LENS SYSTEM WITH NEURAL-BASED CONTROL, naming Eleanor V. Goodall, W. Daniel Hillis, Roderick A. Hyde, Muriel Y. Ishikawa, Edward K. Y. Jung, Nathan P. Myhrvold, and Lowell L. Wood, Jr. as inventors, filed 3 Dec. 2004, now U.S. Pat. No. 7,344,244; a continuation-in-part of U.S. patent application Ser. No. 11/495,167, entitled VISION MODIFICATION WITH REFLECTED IMAGE, naming W. Daniel Hillis, Roderick A. Hyde, Muriel Y. Ishikawa, Edward K. Y. Jung, Nathan P. Myhrvold, Clarence T. Tegreene, and Lowell L Wood, Jr. as inventors, filed 27 Jul. 2006, now U.S. Pat. No. 7,656,569, which is a continuation-in-part of U.S. patent application Ser. No. 11/004,473, entitled VISION MODIFICATION WITH REFLECTED IMAGE, naming W. Daniel Hillis, Roderick A. Hyde, Muriel Y. Ishikawa, Edward K. V. Jung, Nathan P. Myhrvold, Clarence T. Tegreene, and Lowell L. Wood, Jr. as inventors, filed 3 Dec. 2004, now U.S. Pat. No. 7,350,919; a continuation-in-part of U.S. patent application Ser. No. 12/321,560, entitled VISION MODIFICATION WITH REFLECTED IMAGE, naming W. Daniel Hillis, Roderick A. Hyde, Muriel Y. Ishikawa, Edward K. Y. Jung, Nathan P. Myhrvold, Clarence T. Tegreene, and Lowell L. Wood, Jr. as inventors, filed 21 Jan. 2009, now U.S. Pat. No. 7,931,373, which is a divisional of U.S. patent application Ser. No. 11/495,167, entitled VISION MODIFICATION WITH REFLECTED IMAGE, naming W. Daniel Hillis, Roderick A. Hyde, Muriel Y. Ishikawa, Edward K. Y. Jung, Nathan P. Myhrvold, Clarence T. Tegreene, and Lowell L. Wood, Jr. as inventors, filed 27 Jul. 2006, now U.S. Pat. 7,656,569, which is a continuation-in-part of U.S. patent application Ser. No. 11/004,473, entitled VISION MODIFICATION WITH REFLECTED IMAGE, naming W. Daniel Hillis, Roderick A. Hyde, Muriel Y. Ishikawa, Edward K. Y. Jung, Nathan P. Myhrvold, Clarence T. Tegreene, and Lowell L. Wood, Jr. as inventors, filed 3 Dec. 2004, now U.S. Pat. No. 7,350,919; a continuation-in-part of U.S. patent application Ser. No. 11/523,172, entitled METHOD AND SYSTEM FOR ADAPTIVE VISION MODIFICATION, naming Eleanor V. Goodall, W. Daniel Hillis, Roderick A. Hyde, Muriel Y. Ishikawa., Edward K. Y. Jung, Nathan P. Myhrvold, and Lowell L. Wood, Jr. as inventors, filed 18 Sep. 2006, now U.S. Pat. No. 8,244,342, which is a divisional of U.S. patent application Ser. No. 11/004,731, entitled METHOD AND SYSTEM FOR ADAPTIVE VISION MODIFICATION, naming Eleanor V. Goodall, W. Daniel Hillis, Roderick A. Hyde, Muriel Y. Ishikawa, Edward K. Y. Jung, Nathan P. Myhrvold, and Lowell L. Wood, Jr. as inventors, filed 3 Dec. 2004, now U.S. Pat. No. 7,486,988; a continuation-in-part of U.S. patent application Ser. No. 12/072,883, entitled METHOD AND SYSTEM FOR ADAPTIVE VISION MODIFICATION, naming Eleanor V. Goodall, W. Daniel Hillis, Roderick A. Hyde, Muriel Y. Ishikawa., Edward K. Y. Jung, Nathan P. Myhrvold, and Lowell L. Wood, Jr. as inventors, filed 27 Feb. 2008, now U.S. Pat. No. 8,562,540, which is a divisional of U.S. patent application Ser. No. 11/004,731, entitled METHOD AND SYSTEM FOR ADAPTIVE VISION MODIFICATION, naming Eleanor V. Goodall, W. Daniel Hillis, Roderick A. Hyde, Muriel Y. Ishikawa, Edward K. Y. Jung, Nathan P. Myhrvold, and Lowell L. Wood, Jr. as inventors, filed 3 Dec. 2004, now U.S. Pat. No. 7,486,988; and a continuation-in-part of U.S. patent application Ser. No. 12/590,402 entitled VISION MODIFICATION WITH REFLECTED IMAGE, naming W. Daniel Hillis, Roderick A. Hyde, Muriel Y. Ishikawa, Edward K. Y. Jung Nathan P. Myhrvold, Clarence T. Tegreene, and Lowell L. Wood, Jr. as inventors, filed 6 Nov. 2009, now U.S. Pat. No. 8,109,632.

TECHNICAL FIELD

The present application relates, in general, to the field of optical systems for improving and enhancing vision.

BACKGROUND

The use of lenses for correcting vision problems produced by deficiencies in the optical system of the human eye has been known for many years. FIG. 1A illustrates, in schematic form, the anatomy of the human eye 10. Light enters eye 10 through cornea 12, passes through lens 14, and strikes retina 16, the light-detecting inner surface of the eye. The fovea 18 is a central region of retina 16 having particularly high acuity. Lens 14 is attached around its periphery to zonular fibers 20. Zonular fibers 20 are connected to ciliary body 22. Ciliary body 22 is a sphincter muscle which opens when it is relaxed, thereby generating tension in zonular fibers 20. Ciliary body 22 releases tension on zonular fibers 20 when it is contracted. Lens 14, because of its inherent elastic properties, tends to assume a rounded form when it is not subject to external forces. Thus, when ciliary body 22 contracts, lens 14 becomes more rounded, while relaxation of ciliary body 22 produces flattening of lens 14. Cornea 12 provides a significant portion of the refractive power of the optical train of the eye, but the capacity for accommodation is contributed by lens 14.

FIG. 1B illustrates a relaxed (unaccommodated) eye 10, in which lens 14 is flattened. As indicated by the solid lines in FIG. 1B, light from distant objects will be focused on retina 16 (and specifically, on fovea 18) by lens 14, but light from near objects (indicated by the dashed lines) will be focused behind the retina, and thus appear out of focus at the retina. FIG. 1C illustrates an accommodated eye 10, in which lens 14 has assumed a more rounded form. In the accommodated eye, light from near objects (indicated by dashed lines) is focused on retina 16 (fovea 18), while light from distant objects (indicated by solid lines) is focused in front of the retina, and thus is out of focus at retina 16.

In a normal, healthy eye, adjustment of lens 14 is sufficient to focus images on retina 16 within a wide range of distances between the visual target-object and the eye. Myopia (near-sightedness) and hypermetropia (far-sightedness) occur when images entering the eye are brought into focus in front or in back of the retina, respectively, rather than on the retina. This is typically caused by the eyeball being too long or too short relative to the focal-adjustment range of the lens. Eyeglasses with spherical focusing lenses of the appropriate optical refractive power can be used to compensate for myopia or hypermetropia. Another common and readily corrected visual problem is astigmatism, a focusing defect having orientation-dependence about the optical axis of the eye that may be corrected by interposition of a cylindrical lens having appropriate refractive power and axis angle of orientation. Other visual focus problems exist as well (e.g., coma and other higher order optical aberrations), but are less readily characterized and more difficult to correct in a practical manner. In general, focal problems caused by irregularities in the dimensions of the cornea, lens, or eyeball can be corrected providing the optical properties of the eye can be characterized and a suitable set of optical elements manufactured and then positioned relative to the eye.

Aging subjects may experience presbyopia, a decrease in the ability to focus on proximate visual targets caused by reduced flexibility of the eye lens. Difficulty in focusing on such proximate visual targets can be alleviated with the use of 'reading glasses'. Subjects who require correction for myopia as well as presbyopia may use "bi-focal" glasses having lens regions that provide correction for both "near" and "far" vision. The subject selects the type of correction by looking toward the visual target through the appropriate portion of the lens. Elaborations and extensions on such systems are now common, including "trifocal glasses" and "progressive glasses," the latter featuring a continuous gradation in optical properties across a portion of the eyeglass and thus of the visual field thereby regarded.

Adjustable optical systems are used in a wide variety of devices or instruments, including devices that enhance human vision beyond the physiological range, such as telescopes, binoculars, and microscopes, as well as a numerous devices for scientific and industrial applications independent of human vision, such as in test, measurement, control, and data transmission. Such devices typically make use of complex systems of multiple lenses and optical components that are moved with respect to each other to provide a desired level of focus and magnification. Adjustable lens systems that have been proposed for use in eyeglass-type vision enhancement include electroactive lenses, as described in U.S. Pat. Nos. 6,491,394 and 6,733,130 and various types of fluid lenses, as described in U.S. Pat. Nos. 4,466,706 and 6,542,309, as well as assorted multi lens systems (see e.g., U.S. Pat. Nos. 4,403,840 and 4,429,959).

Devices used to characterize certain parameters of the eye optics include phoropters and autorefractometry, as described in U.S. Pat. Nos. 4,500,180, 5,329,322 and 5,629,747. Wavefront analysis systems measure wavefront aberrations produced by the eye optics by delivering an optical signal to the eye that has a well-characterized wavelength and wavefront, and measuring the wavefront reflected from the retina.

Systems for imaging portions of the eye have been developed, such systems including fundus cameras, corneal topographers, retinal topographers, retinal imaging systems, and corneal imaging systems.

Aside from eyeglass—type devices, other systems which present modified visual inputs to the eye include "Virtual Reality" systems, and "heads up displays".

SUMMARY

A method and system for providing adaptive vision modification uses adjustable lens systems. Automatic, real-time lens adjustment may be used to correct the subject's near and far vision during routine activities or to provide vision enhancement beyond the physiological ranges of focal length or magnification in support of specialized activities. Automatic lens adjustment may be based upon detection of the current state of the subject's eye optics. Features of various embodiments will be apparent from the following detailed description and associated drawings.

BRIEF DESCRIPTION OF THE FIGURES

Features of the invention are set forth in the appended claims. The exemplary embodiments may best be understood by making reference to the following description taken in conjunction with the accompanying drawings. In the figures, like referenced numerals identify like elements.

DETAILED DESCRIPTION

In the following detailed description, reference is made to the accompanying drawings, which form a part hereof. The detailed description and the drawings illustrate specific exemplary embodiments by which the invention may be practiced. These embodiments are described in sufficient detail to enable those skilled in the art to practice the invention. It is understood that other embodiments may be utilized, and other changes may be made, without departing from the spirit or scope of the present invention. The following detailed description is therefore not to be taken in a limiting sense, and the scope of the present invention is defined by the appended claims.

Throughout the specification and claims, the following terms take the meanings explicitly associated herein unless the context dictates otherwise. The meaning of "a", "an", and "the" include plural references. The meaning of "in" includes "in" and "on." A reference to the singular includes a reference to the plural unless otherwise stated or inconsistent with the disclosure herein. In particular, though reference is frequently made to "the eye", "the lens" or the "lens system", in most embodiments two lenses or lens systems will be used, one for each eye of the subject, and that, while the operation of the lenses or lens systems will typically be the same, they will typically be adjusted separately to meet the individual needs of the two eyes.

Figure 1A:
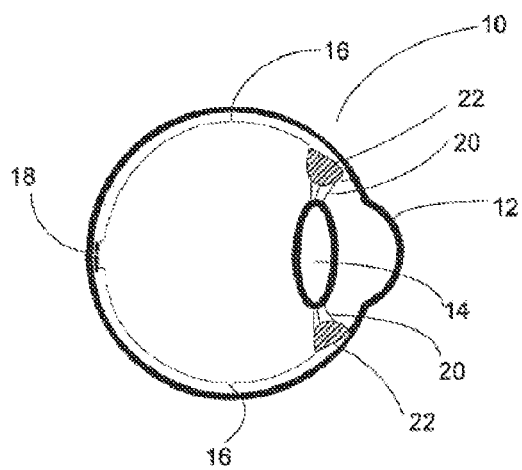
FIG. 1A illustrates the anatomy of the eye.
Figure 1B:
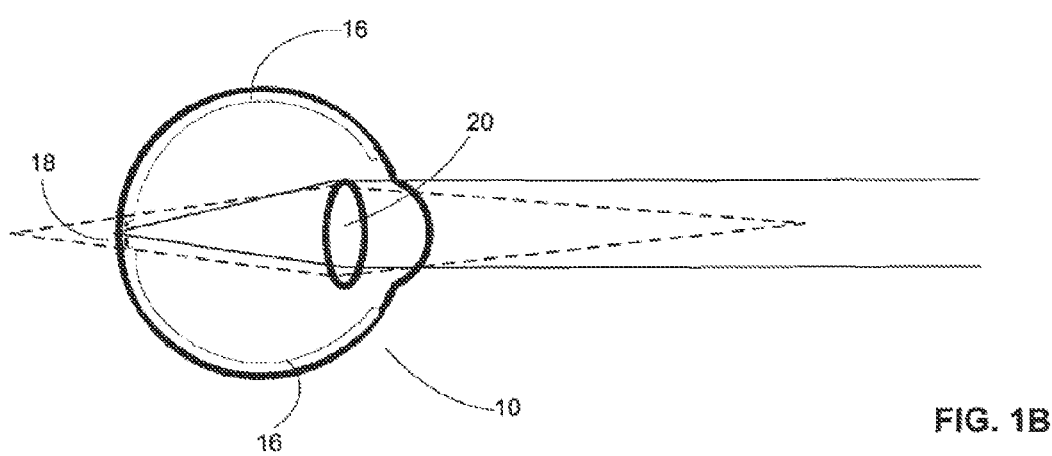
FIG. 1B illustrates focusing of the normal eye for distance vision.
Figure 1C:
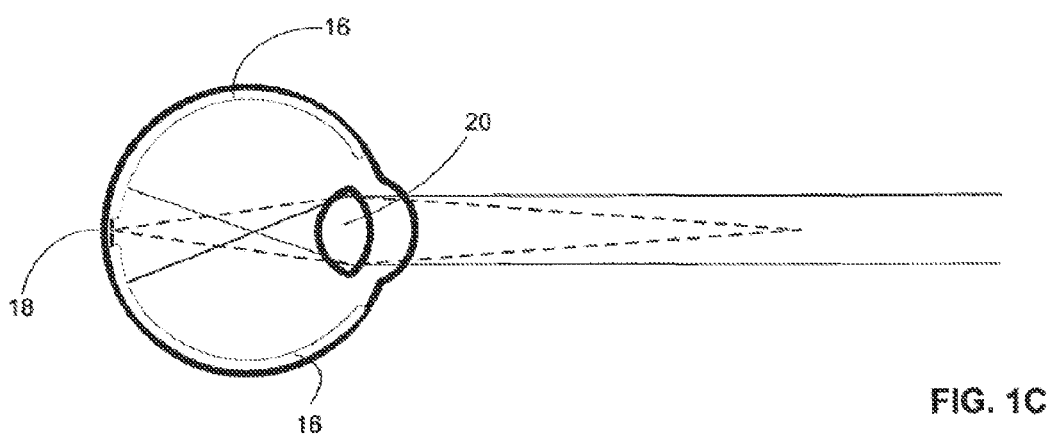
FIG. 1C illustrate focusing of the normal eye for near vision.
Figure 2:
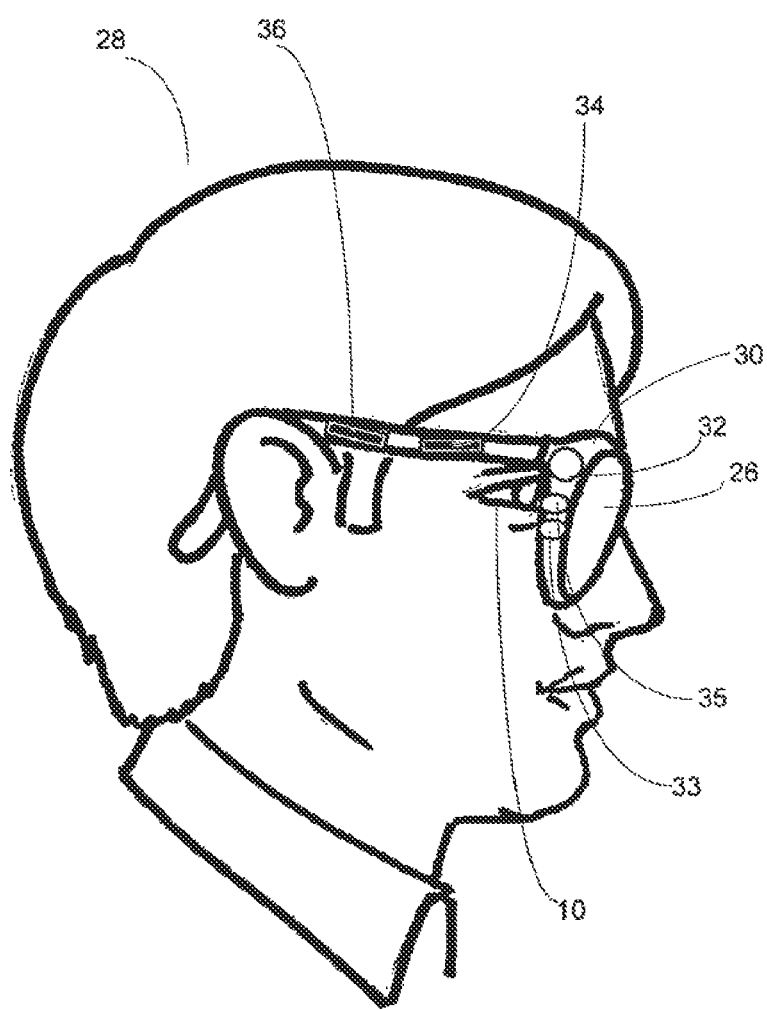
FIG. 2 illustrates an embodiment configured as an eyeglass.

FIG. 2 illustrates the basic components of an exemplary embodiment. Adjustable lens system 26 is positioned with respect to eye 10 of subject 28 through the use of mounting 30, which in this embodiment is an eyeglass frame. Output image detector 32, here mounted on mounting 30, detects an image reflected from eye 10 of subject 28. Input image detector 35 may be provided for detecting an incident image. A light source 33 may be mounted in mounting 30 and used to provide supplemental illumination to the eye during image detection. Note that while a single light source 33 and two detectors 32 and 35 are illustrated, in certain embodiments multiple light sources 33 or detectors 32 and 35 may be positioned in mounting 30. The detected image signal from detector 32 is routed to processor 34. Processor 34 processes the detected image signal to generate a control signal that drives adjustable lens system 26 to provide an enhanced visual input to subject 28. Power supply 36, mounted in mounting 30, provides power to adjustable lens system 26, detectors 32 and 35, light source 33, and processor 34.

Figure 3:
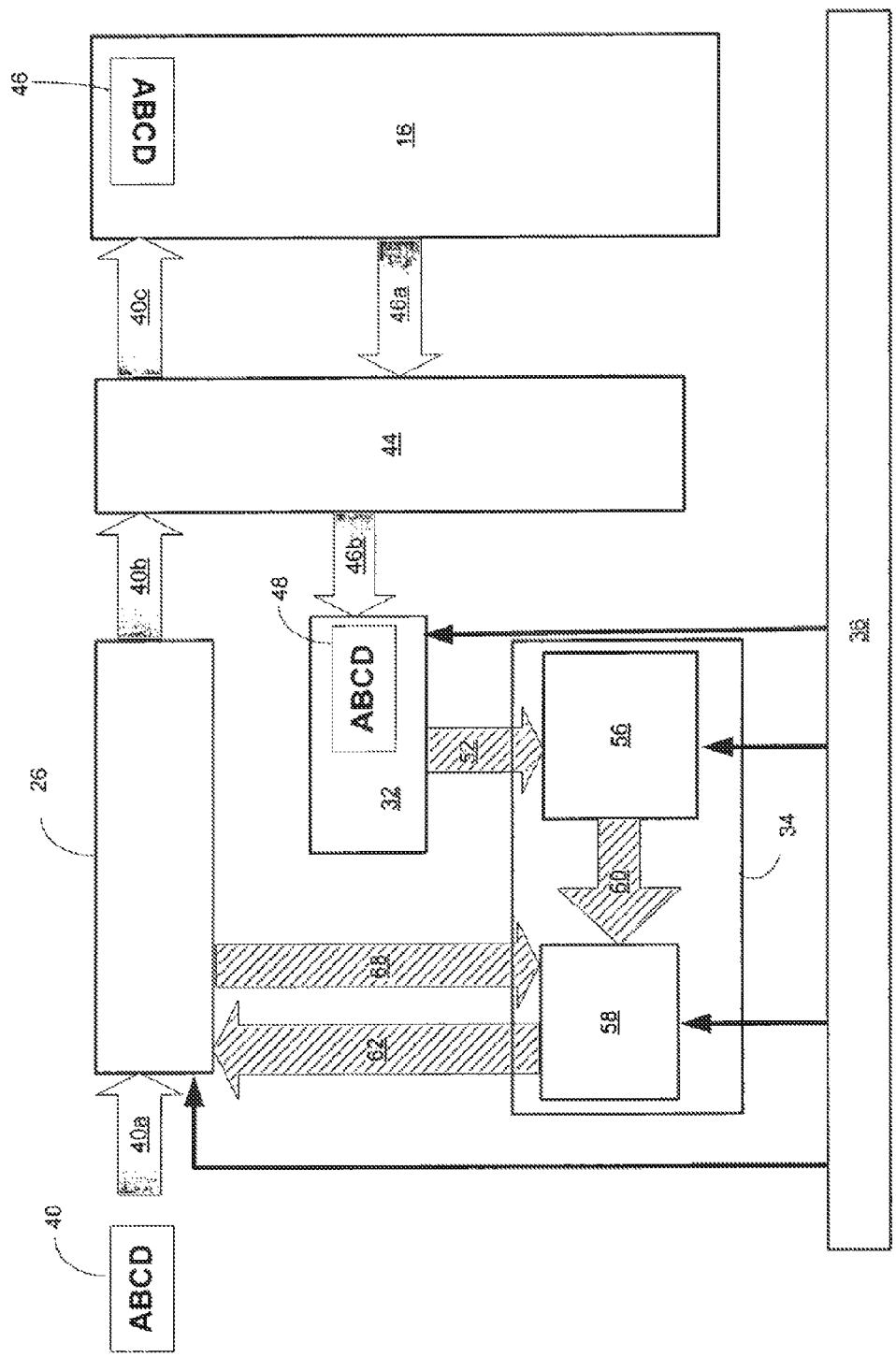
FIG. 3 is a schematic diagram of an embodiment.

FIG. 3 illustrates, in greater detail and in schematic form, components of an embodiment of a system as depicted in FIG. 2. An incident image 40a of a visual target 40 passes through adjustable lens system 26. The incident image is then transmitted through the eye optics 44, which typically include the cornea and the lens of the eye (see intermediate incident images 40b and 40c), and strikes retina 16 to form retinal image 46. Retinal image 46 is reflected back from retina 16, passes back through eye optics 44 (see intermediate reflected images 46a and 46b) where reflected image 48 is detected by output image detector 32. Output image detector 32 creates a representation of reflected image 48 as output image signal 52, which is transmitted to processor 34. The main functional components of processor 34 are image analyzer 54 and lens controller 58. These and other components of processor 34 are discussed in greater detail herein below.

Processor 34 may include various combinations of analog or digital electronic circuitry, discrete components or integrated circuits, and/or hardware, software, or firmware under computer or microprocessor control, including optical analog devices. Processor 34 may include a variety of functional and/or structural components for supporting the function of image analyzer 54 and lens controller 58, such as memory, timing, and data transmission structures and devices. Output image signal 52 is processed by image analyzer 56 to determine the quality of the retinal image. An image quality signal 60 representing the quality of the retinal image is generated by image analyzer 56 and sent to lens controller 58. Lens controller 58 generates lens control signal 62, which is sent to adjustable lens system 26. Adjustable lens system 26. Lens controller 58 may also receive as input a lens state signal 68 from adjustable lens system 26, lens state signal 68 providing information regarding the state of adjustable lens system 26. Lens state information may be used in computations performed by one or both of image analyzer 56 and lens controller 58. Adjustable lens system 26, image detector 32, and processor 34 and its components, image analyzer 56 and lens controller 58, may all be powered by power supply 36. Alternatively, certain components may have separate power sources; the invention is not limited to any particular power supply configuration.

Figure 4:
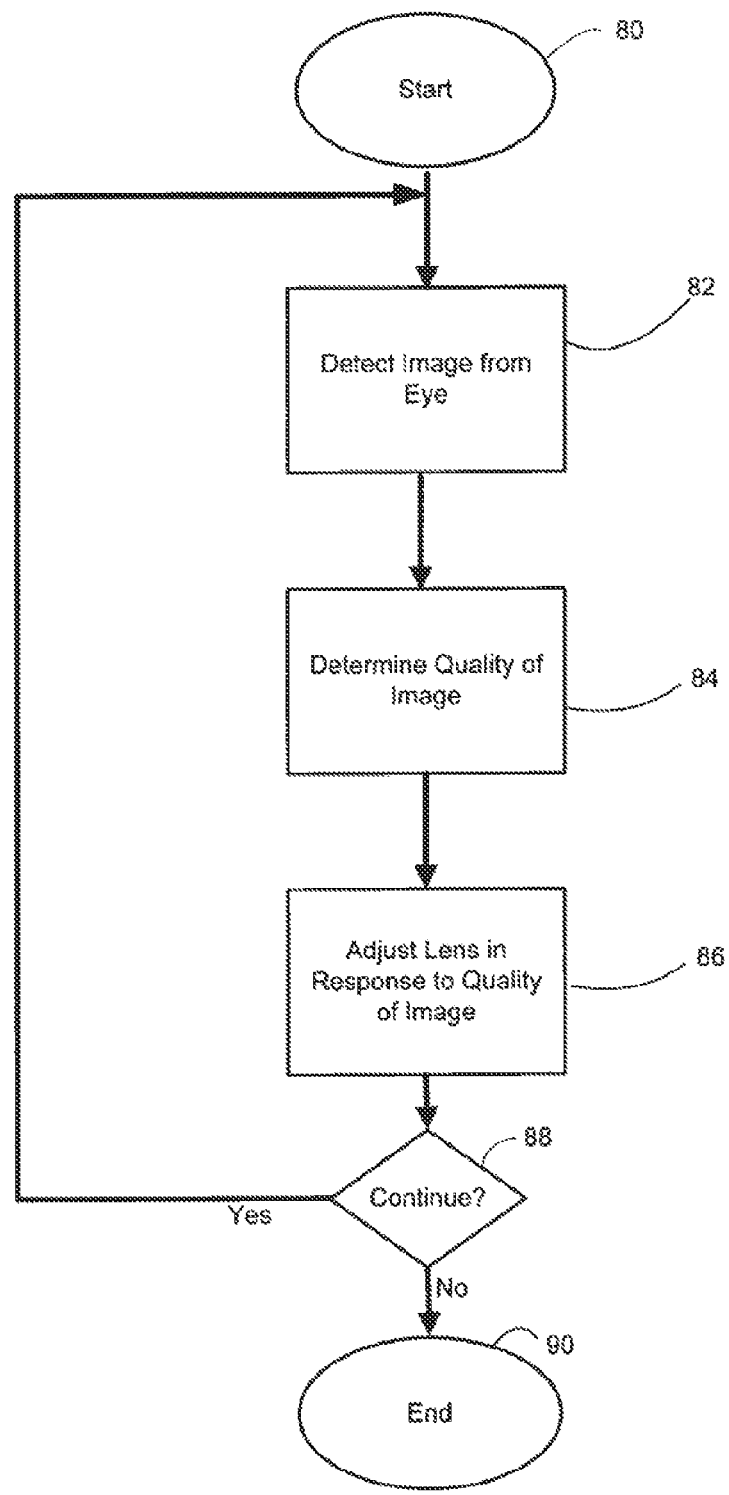
FIG. 4 is a flow diagram of the operation of the embodiment of FIG. 3.

FIG. 4 is a flow diagram showing in general terms the process used by the system of FIG. 3. A reflected image is detected from the eye at step 82. The quality of the detected image is determined at step 84, and the adjustable lens system is adjusted in response to the determined quality of the image at step 86. In order to provide on-going adaptive vision modification, after step 86, at branch point 88, control returns to step 82 and steps 82 through 86 are repeated for as long as adaptive vision modification is desired.

Figure 5:
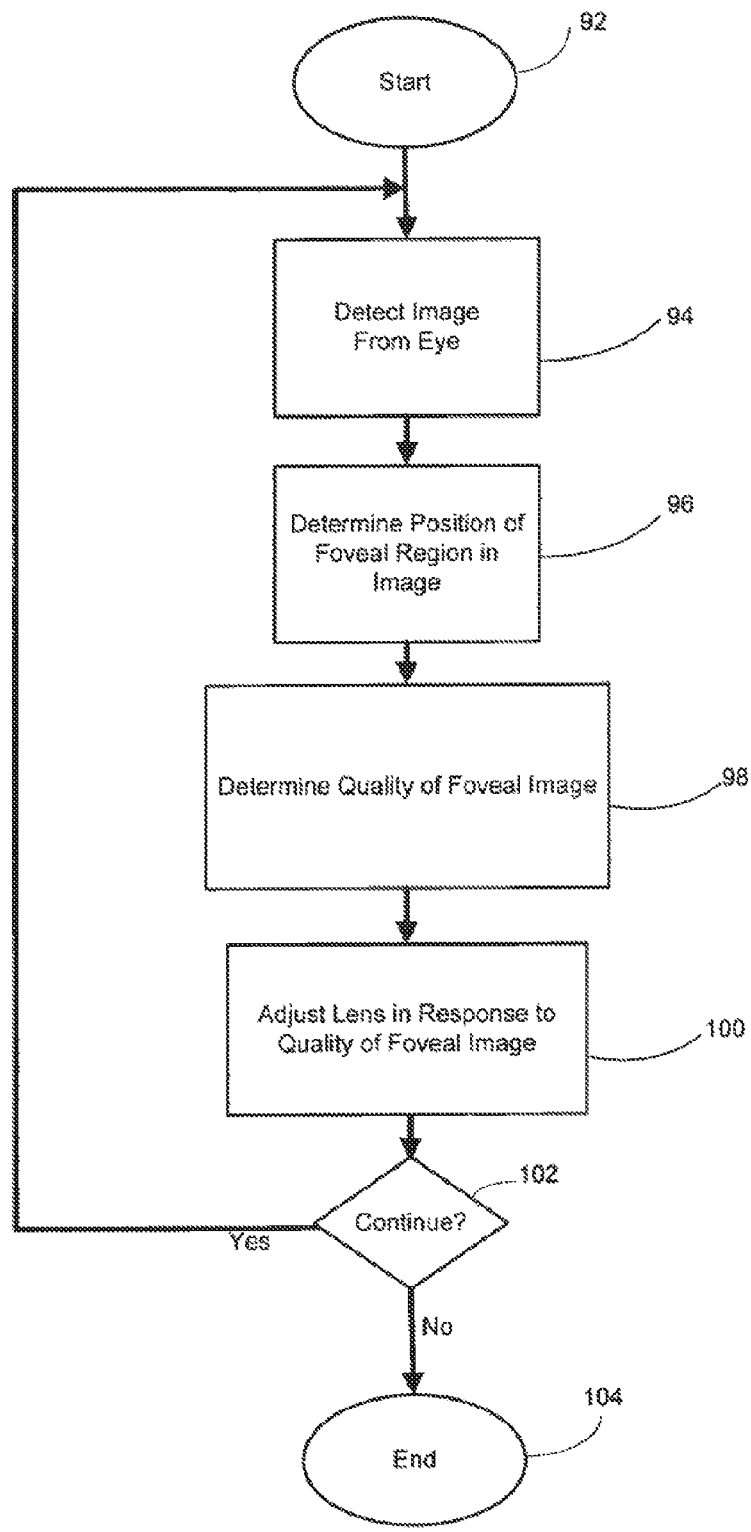
FIG. 5 is a flow diagram of an alternative implementation of the embodiment of FIG. 3.

FIG. 5 depicts a variant of the process diagrammed in FIG. 4. The reflected image is detected from the eye at step 94. Rather than determine the quality of the entire retinal image, the position of the fovea within the image is determined at step 96, and the quality of the foveal image is then determined at step 98. At step 100, the lens system is adjusted in response to the quality of the foveal image. At branch point 102, if ongoing adaptive vision modification is to be provided, process control returns to step 94 and steps 94 through 100 are repeated to provide on-going adaptive vision modification.

Figure 6:
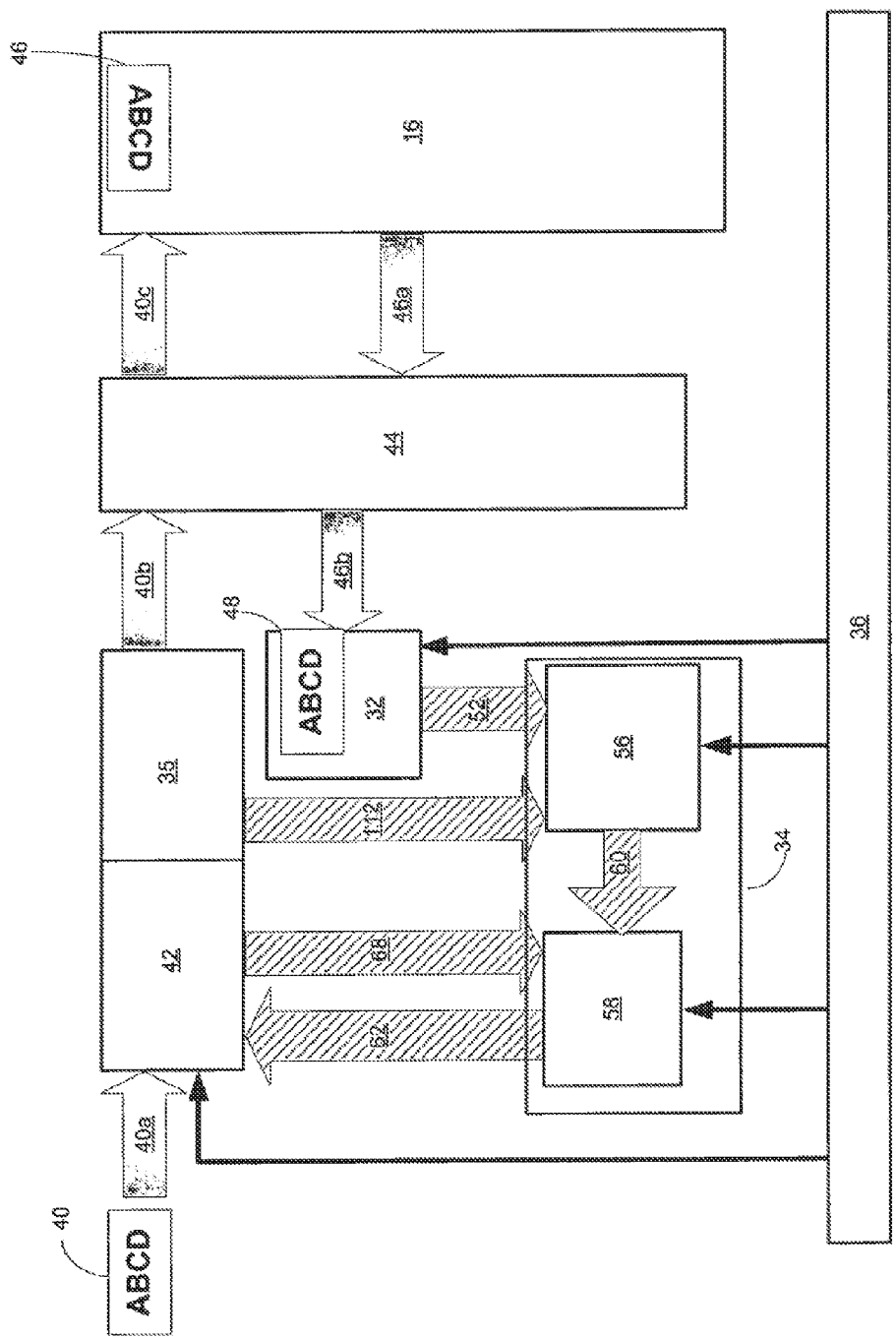
FIG. 6 is a schematic diagram of another embodiment.

FIG. 6 illustrates, in schematic form, functional components of a second embodiment. As in the embodiment depicted in FIG. 3, incident image 40*a* passes through adjustable lens system 42. Incident image 40*a* is detected by input image detector 35; intermediate incident image 40*b* subsequently passes through eye optics 44 to retina 16. Retinal image 46 is reflected from retina 16, passes back through eye optics 44 (see reflected images 46*a*, 46*b*) to form reflected image 48 which is detected by output image detector 32. Input image detector 35 creates a representation of incident image 40 as input image signal 112, while output image detector 32 creates a representation of reflected image 48 as an output image signal 52. Input image signal 112 and output image signal 52 are both transmitted to image analyzer 56 in processor 34, where the image data is processed to obtain a comparative measure of the quality of the retinal image.

Figure 7:
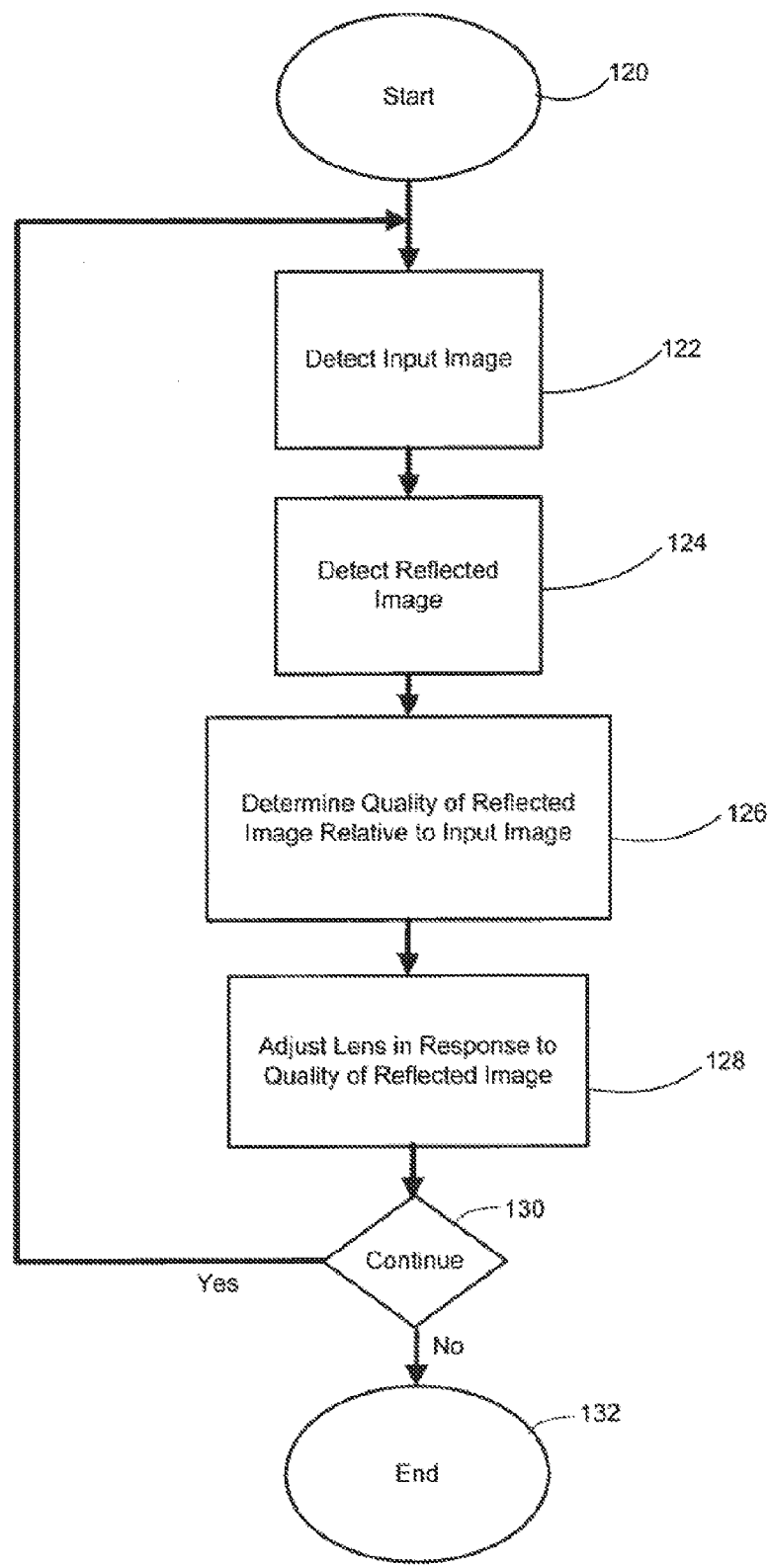
FIG. 7 is a flow diagram of the embodiment of FIG. 6.

FIG. 7 is a flow diagram of the control flow used by the system of FIG. 6. An input image is detected at step 122, and a reflected image is detected at step 124. The quality of the output (reflected) image relative to the input (incident) image is determined at step 126, and the adjustable lens system is adjusted in response to the determined quality of the reflected image at step 128. At branch point 130, control returns to step 122, and steps 122 through 128 are repeated for as long as desired to provide on-going adaptive vision modification.

Figure 8:
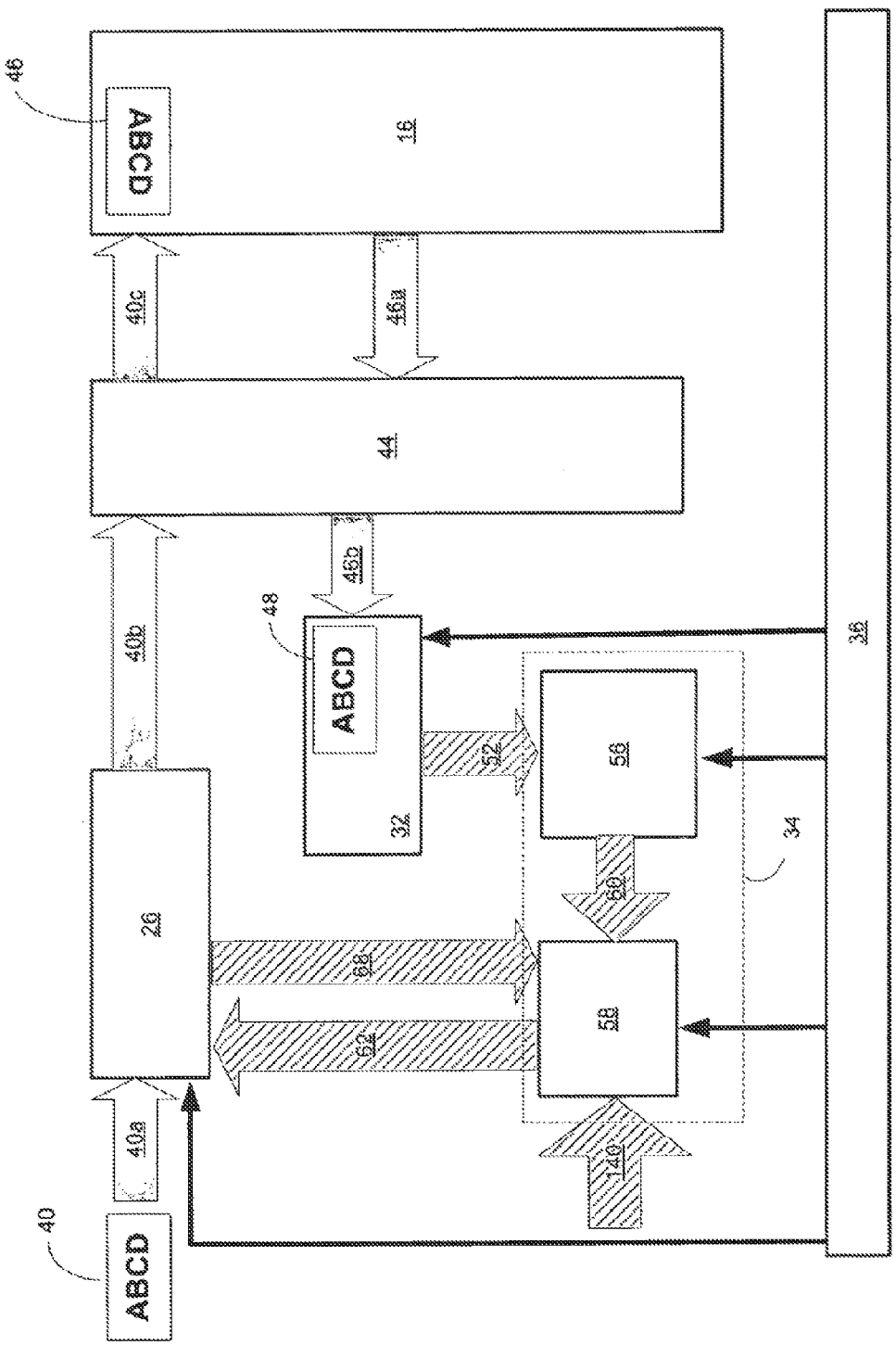
FIG. 8 is a schematic diagram of a further embodiment in which a magnification factor input is accepted.

FIG. 8 is a schematic diagram of a further embodiment suited for certain specialized applications requiring image magnification outside the physiological range of human vision. As in the embodiment illustrated in FIG. 3, an incident image 40*a* passes through adjustable lens system 26. Intermediate incident image 40*b* is transmitted through the eye optics 44 and strikes retina 16 to form retinal image 46. Intermediate reflected image 46*a* passes back through eye optics 44 to form reflected image 48 at output image detector 32. Output image detector 32 detects reflected image 48 and generates a representation of it as output image signal 52, which is transmitted to processor 34. Output image signal 52 is processed by image analyzer 56 to determine the quality of the retinal image. An image quality signal 60 representing the quality of the reflected image is generated by image analyzer 56 and sent to lens controller 58. Processor 34 is adapted to also receive a magnification factor input 140. Magnification factor input 140 may be entered into processor 34 by various methods; it may be preprogrammed at a fixed value or entered by the subject. It is contemplated that the magnification factor will be used for special applications (e.g., close-up detail work or viewing distant objects) and that the subject may prefer to adjust the magnification to meet the requirements of a particular application. Manual selection of the magnification factor may be accomplished, for example, by configuring the device with one or more preprogrammed magnification factor values, and having the subject press a button on the eyeglass frame to cycle through magnification values until arriving at the desired magnification value; clearly, provision also may be made for continuously-variable magnification control. Alternatively, the magnification factor may be determined adaptively, e.g. by calculation of the magnification necessary to expand a detected visual target to fill a selected percentage of the users field of view.

As shown in FIG. 8, taking into account magnification factor input 140, lens controller 58 generates lens control signal 62, which is sent to adjustable lens system 26. Lens controller 58 may also receive as input a lens state signal 68 from adjustable lens system 26, which provides information regarding the current state of adjustable lens system 26.

Figure 9:
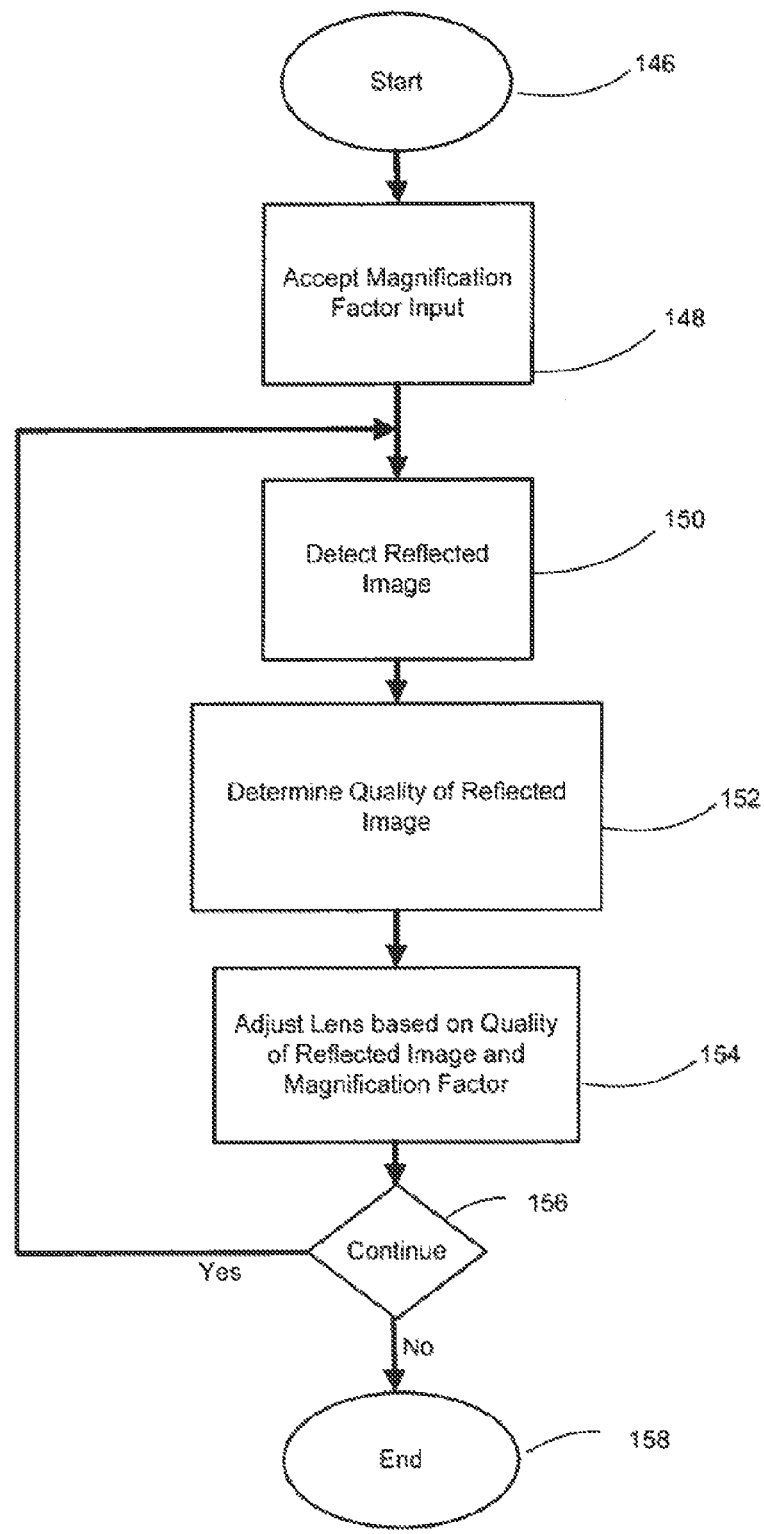
FIG. 9 is a flow diagram of the use of the embodiment depicted in FIG. 8.

FIG. 9 is a flow diagram of the process used for controlling the embodiment depicted in FIG. 8. The magnification factor input is accepted at step 148, either by detecting a user-entered value, reading a stored or calculated value from a memory location, or by other mechanisms known to those of skill in the art. The main process loop is then entered. The reflected image is detected at step 132, the quality of the reflected image is determined at step 152, and the lens system is adjusted based on the quality of the reflected image and on the magnification factor at step 154. At branch point 156 process control returns to step 132 and steps 132 through 154 are repeated to provide on-going adaptive vision modification for as long as vision modification at the selected magnification is desired. Note that the process depicted in FIG. 9 may be part of a larger process, and that by including additional control loops, it would be a simple matter to provide for the input of an updated desired magnification factor value, during an ongoing control process.

As illustrated by the foregoing examples, the exemplary systems comprise a number of basic components, the structure and operation of which will now be described in greater detail. As illustrated in FIG. 2, these components are: an adjustable lens system 26, one or more image detectors (image detector 32, as shown in FIGS. 3 and 6, and input image detector 35 as shown in FIG. 6); processor 34, which includes an image analyzer 56, and lens controller 58, as shown in FIGS. 3 and 6; and power supply 36.

Various types of adjustable lens systems may be used in practice, and the invention is not limited to any particular type of adjustable lens system. However, certain adjustable lens systems may be more suitable than others, with small size, low weight, rapid adjustment, and compatibility with other system components being considerations for some applications. Depending on the particular intended application, certain considerations may be of greater importance than others, and thus the best choice of lens system will vary from application to application. While in some cases a single lens may be used, the term "lens system", as used herein, refers to systems made up of one or more lenses and, optionally, additional optical elements or components including but not limited to reflectors, beam splitters, refractive elements, active and passive filters, and so forth.

Conventional eyeglass lenses and contact lenses are typically characterized by their spherical lens strength or optical power (typically expressed in positive or negative diopters, the reciprocal of their focal length measured in meters-distance), cylindrical lens strength, and cylindrical axis orientation. Lenses may modulate the spatial frequency content of an image formed thereby (e.g., by adjusting the focus of the image) and may also modulate the light intensity of the image as a function of wavelength, by spectrally-dispersive properties of their bulk composition or coatings applied to their surfaces, for example. Suitable adjustable lens systems may be characterized by these and additional focus or image-quality parameters. Lens systems may be used to provide image magnification outside the physiological range of human vision, and hence may be characterized by a magnification strength factor as well. An adjustable lens system used to provide vision correction may preferably permit the adjustment of each of these parameters, although in particular applications and for particular subjects, not all of these parameters may need to be adjusted. Independent adjustment of each of the various parameters may be desirable in some cases, but in many cases may not be required.

A number of designs for fluid-based adjustable lenses have been proposed which may be suitable for use. Fluid lenses utilize one or more fluids having appropriately selected indices of refraction. One approach is to enclose fluid within a deformable shell, and to increase fluid volume or pressure to deform the shell and thus change the optical strength of the lens, as disclosed in U.S. Pat. Nos. 4,466,706, 5,182,585, 5,684,637, 6,069,742, 6,542,309 and 6,715,876, which are incorporated herein by reference. Another approach is to utilize two immiscible liquids of differing refractive properties contained within a chamber, and modify the shape of the fluid-fluid interface in order to change the optical strength of the lens. The surface tension properties of the interior of a chamber are modified, for example, through an applied voltage (and thus electric field and gradients thereof) to adjust the shape of the fluid-fluid interface. Such fluid lenses, as disclosed in U.S. Pat. No. 6,369,954, which is incorporated herein by reference in its entirety, may also be suitable for use in some embodiments.

Another suitable type of adjustable lens system may be an electro-active lens as described in U.S. Pat. Nos. 4,300,818, 6,491,394 and 6,733,130, also incorporated herein by reference. These lenses include one or more layers of liquid crystal or polymer gel having refractive power that may be modulated, e.g. electrically. An advantage of this type of lens is the refractive power can be adjusted selectively in different regions of the lens, making it possible to produce nearly any desired lens, including a lens that compensates for higher order optical aberrations, or a lens having regions with different focal strengths (comparable to a bi-focal or tri-focal lens), such that all or a portion of the lens can be adjusted. It is also possible to construct a lens system that can be rapidly switched from one focal length to another with the use of this technology.

In some embodiments, an adjustable lens system may be made up of multiple lenses or other optical elements. Lens system adjustment may include moving one optical element with respect to another or with respect to the subject. Such movements may include one or all of changing the distance, angle-of-orientation, or off-axis displacement between two or more optical elements. The adjustable lens system may include a lens mechanism and a lens actuator that is used for actuating the lens mechanism. Thus, the lens mechanism itself may not receive control signals directly from the lens controller. The lens mechanism and lens actuator may be formed integrally, or they may be separate elements depending on the design of the lens system.

As used herein, "lens system" refers to systems made up of one or more lenses and, optionally, additional optical elements or components including but not limited to reflectors, beam splitters, active and passive filters, and so forth. An "adjustable lens system" is a lens system in which one or more optical properties of the system can be adjusted. Adjustable lens systems may modify incident light in some specified matter. Adjustable lens systems may bend (refract) incident light rays; they may also filter the incident light to modify the spectral composition of the incident light or to change the light intensity at one or more selected spectral wavelengths or wavebands.

As used herein, the term "optical system" is defined generally to mean a system that is capable of modifying an incident image or pattern of light to produce a modified image or pattern of light. In a broad sense, an optical system may be any device or system that receives an input image and produces an output image that is a modified version of the input image. As such, optical systems may include lens systems. In addition, in certain embodiments the modified image is not formed entirely or even in significant part of incident light that has been transmitted through the optical system, but partly or mostly (including entirely) of light that has been generated by the optical system to form a new image. In some embodiments, the term 'optical system' may encompass systems including cameras and displays. Such an optical system may modulate the input image in ways not possible with lenses or lens systems that transmit incident light; e.g., the optical system may transform the incident image by shifting the spectral content or intensity of some or all wavelengths relative to the incident light corresponding to the image. Adjusting either lens systems or optical systems may include adjusting one or more focal lengths, adjusting one or more cylindrical corrections, adjusting one or more distances of an optical element relative to an eye of the subject or adjusting the orientation-angle of the optical element with respect to the optical axis of the eye or adjusting the off-axis displacement of one or more optical elements relative to the optical axis of the eye or adjusting the pan-or-tilt of one or more optical elements relative to the optical axis of the eye.

One or more image detectors or sensors may be used for detecting images reflected from the eye and, in some embodiments, input (incident) images impinging on the eye. A number of existing technologies may be suitable for performing image detection, and the practice is not limited to any particular type of image detector. Suitable detectors include those of the type used in retinoscopes, phoropters, autorefractors, and the like, and particularly those which are capable of providing rapid image update rates. The term "image detector", as used herein refers to devices or systems capable of detecting an image of the eye, and is intended to encompass detection systems that include one or more individual light detecting elements in combination with other optical system components, such as scanning mirrors, lenses, controllers, and data acquisition or storage elements. Examples of suitable detectors include CCD cameras or systems based on photodiodes or photomultipliers. See for example, the image detection systems described in U.S. Pat. Nos. 6,227,667 and 6,523,955, which are incorporated herein by reference. Image detectors may detect light signals from multiple positions in an imaged area of the eye simultaneous or sequentially. Sequential detection systems may employ either one or both of a detector and an illumination source that are scanned across the area to be imaged, as described in U.S. Pat. No. 6,227,667. While in some cases it is preferred that detection is performed without providing supplemental illumination to the eye of the subject, in certain embodiments, supplemental illumination of the eye may be provided by a light source 33 as depicted in FIG. 2, which may be, for example, an IR laser. Supplemental illumination is preferably outside the visible range and must be of an intensity that is not harmful to the eye. Use of supplemental illumination during retinal imaging is known to those of skill in the art.

Image detectors can be positioned in or on the mount in which the corrective lens is mounted as depicted in FIG. 2, or in or on the lens itself. Image detectors can be positioned in or on a contact lens, or intraocular lens device as well as an eyeglass lens, by using suitable microfabrication techniques. Methods for microfabrication of optical components such as photodiodes and mirrors are known in the art (see, e.g. U.S. Pat. Nos. 5,306,926, 5,629,790, 6,177,800, 6,379,989, 6,399,405, 6,580,858, 6,658,179, 6,744,550, and 6,762,867, which are incorporated herein by reference in their entirety). The image detector may be formed separately from the lens system or mounting and subsequently attached thereto, or formed integrally with the lens system or mounting. Detectors for detecting images reflected from the retina or other structures within the eye will preferably be directed toward the eye of the subject, e.g., by forming the detectors on the inner surface of the corrective lens. Conversely, detectors for detecting incident (input) images may preferably be directed outward with respect to the eye, e.g., by forming the detectors on the outer surface of the corrective lens. However, the invention is not limited to any particular sensor position or orientation, since additional optical elements (mirrors, prisms, lenses, etc.) may be used to direct the image to the sensor for any given sensor placement.

The image detector may be located at a distance from the image analyzer, and detected image signals transmitted to the image analyzer by a transmitter. In this case, the image analyzer can also function as a receiving location, and may include a receiver for receiving the image signal transmitted by the detector. The image detector may detect at least one component of a finite fraction of a time-varying image. A component may include, but is not limited to, a wavelength band component, a spatial frequency component, a spatial or areal component, or other detectable or determinable components of an image or portion of an image. The terms "finite fraction" or "portion", as used herein, refer to a part, portion, fraction, or percentage of something (in this case, an image), up to and including 100 percent or the entirety of the thing in question.

While discussion herein is focused on detecting images reflected from the retina of the eye (also known as "retinal reflex" images), i.e., "output image signal" the approaches herein are also considered to include systems in which images reflected from other structures within the eye are measured in order to determine the current optical properties of the eye, and particularly the lens, and control the quality of the image on the retina. For example, it would also be possible to measure an image reflected from the back surface of the eye lens, and to calculate the image at the retina based upon knowledge of the dimensions of the eye and the optical characteristics of the medium (the vitreous humor) filling the space between the lens and the retina. In certain embodiments, it may be advantageous to detect images reflected from several locations within the eye and utilize the differential image information to determine the optical properties of the eye. Thus, the input or reference image may not be an incident image detected from a location external to the eye, as described above, but may be an image detected from within the eye. For example, images reflected from the cornea or the front surface of the lens may be detected. The approaches herein are not limited to use of images detected from any specific location. If images are detected from more than one region of the eye, two or more separate image detectors may be used. Alternatively, one detector may be used to detect images from two or more locations in the eye, using reflectors or other optical elements to switch between the different locations.

As illustrated in FIG. 3, the main functional components of processor 34 are image analyzer 56 and lens controller 58. Processor 34 may include various combinations of analog or digital logic circuitry in the form of discrete components or integrated circuits, hardware, software, and/or firmware under computer or microprocessor control. Processor 34 may also include various functional and/or structural components such as memory, timing, and data processing, transmission, and reception structures and devices necessary to support the operation of image analyzer 56 and lens controller 58. It will be recognized by one skilled in the art that the functions and operation of Processor 34 may be implemented in software, in firmware, in special purpose digital logic, or any combination thereof, and that the design of processor 34 to perform the image analysis and lens control tasks described below may be performed in various ways by a practitioner of ordinary skill in the relevant art. Digital signal processing (DSP) chips or devices suitable for image processing are commercially available or may be designed for specific applications. Processor 34 may be implemented in hardware (e.g. as an Application Specific Integrated Circuit) to minimize size and weight of the system while maximizing speed of operation. Alternatively, some portions of processor 34 may be implemented in software running on a microprocessor-based system. This will provide greater flexibility, relative to specialized hardware, but system size and weight generally will be increased. Although processor 34 (including image analyzer 56 and lens controller 58) may be packaged as a single unit, in some cases it may be preferable to package certain components separately. For example, as discussed previously, processor 34 may include a receiver for receiving an image signal transmitted from a detector and a transmitter for transmitting control signals to the adjustable lens system.

Tasks performed by the image analyzer may include a variety of manipulations of one or more image signals, including preprocessing steps such as detection of the relevant regions of the detected image, processing to increase the signal-to-noise ratio, and analysis of the image to determine values of selected image quality metrics. While the full range of image processing tasks may be performed by the image analyzer in some embodiments, in other embodiments, selected pre-processing steps may be performed by appropriately configured image detector(s).

Depending on the position and configuration of the image detector(s), the detected image may include portions (e.g., of the subject's eye and face) that are not of interest. Therefore, image preprocessing may include selecting for further analysis only those portions of the detected image that are of interest, e.g. the retina, or more particularly the fovea. Selection of areas of interest may be based on light intensity thresholding (to remove areas of the image outside the pupil of the eye), or feature detection. The position of the fovea in the image may be tracked in some embodiments. Landmarks that may be used to detect and track selected portions of the retina, and particularly the fovea, include the optic nerve and certain blood vessels. Such techniques are well known to those of skill in the art of retinal imaging.

Image manipulations to improve the signal to noise ratio or otherwise make the detected image easier or more convenient to work with may include a variety of conventional image processing techniques, such as filtering, noise reduction, adjusting offset and scaling, contrast enhancement, spatial "cropping", spectral (color) selectivity, selection of at least portion of a detected image for further analysis, or various mathematical transformations, such techniques being known to those with skill in the art.

After preliminary image processing steps have been completed, the processed image is analyzed to obtain one or more measures of image quality. The term "image quality" as used herein, means any of various parameters, also referred to as "image quality attributes" or "image quality metrics" or "image metrics" that may be used to characterize the image or a portion of the image, particularly with regard to meaningful or useful content. The term "quality" is not intended to imply "good quality" or "high quality" but rather quality in general, whether good, bad or mediocre.

Image sharpness, or fineness-of-focus (i.e. sharpness or 'crispness' of focus), is an important measure of image quality. Image focus may be broken down into a number of components thereof, such as spherical focus or cylindrical focus (with an associated axis of orientation). Choice of quality metric in certain embodiments may be matched to the attributes of the optical aberrations that can be corrected by the adjustable lens system or optical system. In some cases, detecting (and subsequently correcting) only one focal attribute may be performed. In other cases, multiple focus attributes may be detected and corrected.

Image sharpness or focus is not the only measure of image quality. Depending on the intended application of the system, other image attributes or quality metrics may be considered of greater interest or importance. These may include metrics such as for, example, image contrast or intensity.

Image quality may be assessed from the entire selected image (meaning the entire retina image or a selected region of the retina, for example, the fovea), or it may be assessed from selected features of the image, e.g. the optic nerve or a blood vessel. One method that may be used for assessing the image as a whole is to perform a frequency domain analysis of the image. The human visual system is particularly tuned to and responsive to edges and areas of high contrast. Frequency domain analysis of an image reveals that the amplitude of high spatial frequency components is relatively higher in such areas. An in-focus image will generally have a relatively higher frequency composition than an out-of-focus image, and therefore, spatial frequency content may also serve as an indicator of image focus. Therefore, the amplitude of selected high spatial frequency components could be used as a metric of image quality. The peak spatial frequency content may be of particular value. Frequency compositions may be determined, for example, by using a FFT (Fast Fourier Transform). The Fourier transform is only one example of a variety of well-known transformation methods that may be used for performing a frequency domain analysis of an image signal, and that may provide useful measures of image quality suitable for use in the practice of the methods and systems described herein.

As an alternative to (or in addition to) performing a frequency analysis of an image or portion of an image, image analysis may include a preliminary step of feature identification followed by a calculation of the degree of sharpness (or "focus") of that feature. For example, the feature may be an edge or a light-dark transition, and the sharpness may be quantified by the amplitude of the light-dark transition, for example. Various other detectable features and measures of feature sharpness are known in the art of image processing.

In embodiments of the inventive system in which only the output (reflected)) image is detected, image quality is determined self referentially; since the visual input is not known, it is assumed that certain features of the visual input (e.g. lines, edges) have predictable characteristics. Deviations from the expected characteristics in the reflected image may indicate an out-of-focus retinal image, and the need for adjustment of the adjustable lens system to compensate for aberrations in the eye optics. In embodiments in which both input (incident) and output (reflected) images are detected, the difference between the input and output image provides further information regarding the characteristics of the eye optics and need for adjustable lens system adjustment. The reflected image can be compared to a reference image other than the input image. It is sufficient that the reflected image and reference image be detected at different locations in the visual train, such that the difference in the two images is caused by the eye lens (and/or other components of the eye optical system for which correction is sought). Determination of the difference between the reflected image and the reference image may be determined by calculating a difference signal and then computing one or more image quality attributes for the difference signal, or by determining one or more image quality attributes for each of the reflected and reference image, and comparing the image quality attributes for the two images.

In some cases, information derived from the output image alone, or the combination of the input (reference) and output image, will be sufficient to determine the necessary adjustment of the adjustable lens system. In other cases, analysis of the available images may not be sufficient to determine the optimal direction and magnitude of lens system adjustment. In such cases, an adaptive algorithm for lens system adjustment may be used, in which the lens system is adjusted and the quality of the retinal image before and after the lens system adjustment is compared. In this case, the reference image may be a previous instance of the time varying image detected from the retina or fovea. As discussed previously, comparison of current and previous (reference) images can be based on determination of image quality or focus attributes for the difference signal, or comparison of image quality or focus attributes for the two signals. The direction and magnitude of lens system adjustment steps may then be modified based upon the result of the previous adjustment. First and second time varying images can thus occur at different "locations" in at least one of space, time, or spectral position.

Processor 34 may utilize image analyzer 54 to process signal data from detector 32 to generate a transfer function for the current state of the optical system of eye 10, and then utilize lens controller 58 to modify the transfer function of adjustable lens system 26 by sending an appropriate control signal to adjustable lens system 26 such that the eye optical system and adjustable lens system together cause a desired representation of the external visual world to be formed on the retina. In most cases, but not all, a clear, in-focus, image on the retina is desired; however, in some cases adjustable lens system 26 may be controlled to modify the retinal image in some particular way relative to the external visual world. Such modification may include changes in magnification (beyond the normal change in modification produced by the optical system of eye 10), changes in spectral content, and changes in focal length.

Figure 10:
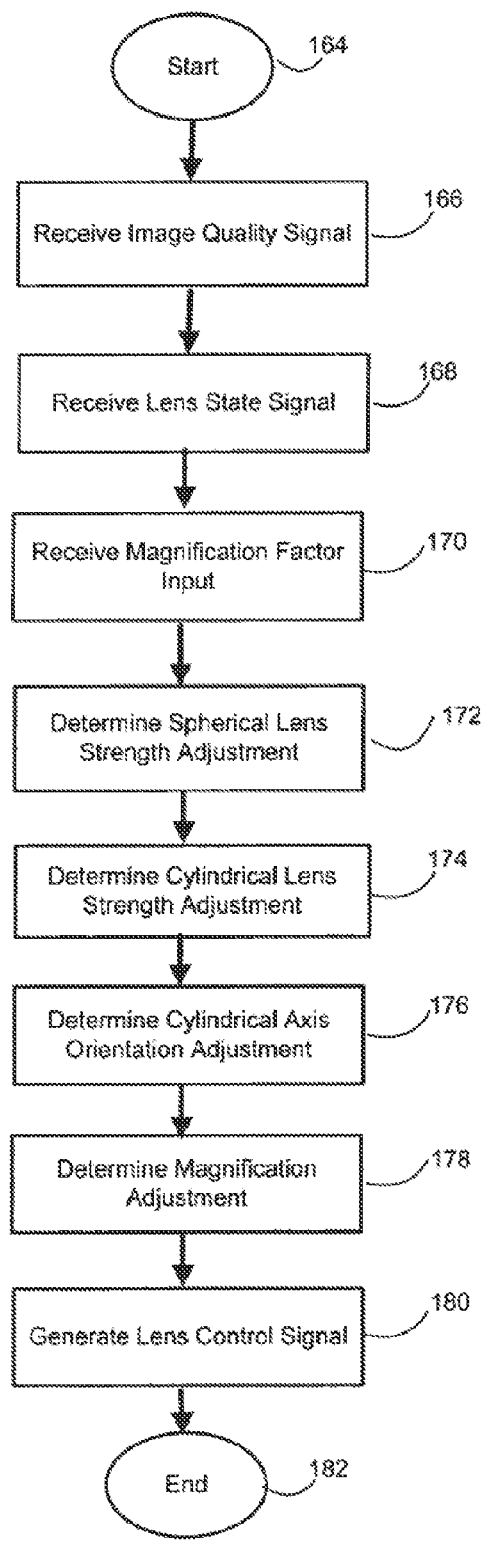
FIG. 10 is a flow diagram of lens adjustment steps.

FIG. 10 breaks down into greater detail an exemplary lens control process as it may be performed by lens controller 58 (in other words, the process performed at step 86 in FIG. 4, step 100 in FIG. 5, step 128 in FIG. 7, and step 154 in FIG. 9). At step 166, processor 34 receives image quality signal 60. At step 168, processor 34 receives lens state signal 68. At step 170, processor 34 receives magnification factor input 140, which may be a stored value. Steps 166, 168, and 170 may be performed in any desired order; moreover, in some applications certain of the received parameters may not be adjusted, so the parameter value may be a stored constant value, or the step of receiving a magnification factor value may be omitted entirely. Subsequently, processor 34 (specifically lens controller 58) determines a spherical lens strength adjustment at step 172, determines a cylindrical lens strength adjustment at step 174, determines a cylindrical axis orientation adjustment at step 176, and determines a magnification adjustment at step 178. Steps 172, 174, and 176 may be performed in other orders than depicted in FIG. 10; if one or more of the parameters are not adjusted, one or more of steps 172, 174, and 176 may be omitted as appropriate. At step 180, lens controller 58 generates a lens control signal based upon the adjustments determined in steps 172, 174, and 176. Depending on the nature of the adjustable lens system and lens actuation scheme, the control signal may reflect newly determined absolute settings for the adjustable lens system, or the control signal may reflect changes to lens system settings relative to the current lens system settings. Adjustable lens system settings may be adjusted to modify various measures of image quality, including image sharpness or focus, image spatial frequency content, or any other selected image metric or image quality attribute. Modification of the adjustable lens system settings may be selected to move one or more image metrics or quality attributes toward a specific target value, in a desired direction, or simply to produce a change in the image metric or quality attribute which may be used as a reference value in an adaptive control algorithm. Determination of lens system adjustment may be performed using known principles of control system design. For example, an exemplary method for adjusting a lens system in response to the quality of a detected image may include determining an adjustment direction in response to the determined spatial frequency content and then adjusting the lens system in the determined adjustment direction. Determining the adjustment direction may include determining a change in the sharpness caused by adjusting the lens system in the determined adjustment direction by determining the sharpness of a previous instance of the image, and determining further change to the lens system adjustment based on the result of the previous adjustment. For example, if the previous adjustment produced a reduction in image sharpness, the direction of lens system adjustment may be reversed. Conversely, if the adjustment increased image sharpness, the next adjustment step may be in the same direction. Various lens system parameters (spherical focus, cylindrical focus, etc.) may be adjusted independently, and the determination of adjustment of each lens system parameter may be responsive to different image quality attributes. In some embodiments, image quality may be measured in a selected region of the image (e.g., the fovea) and a lens system adjustment selected to optimize the foveal image applied to the entire lens, thus modifying the focus over the entire retina. In other embodiments, the focus may be adjusted separately for areas of the adjustable lens projecting onto different regions of the retina. These and other approaches for controlling lens system adjustments may be performed by an appropriately configured or programmed lens controller, and may involve the controlled use of a lens system having other than purely spherical or cylindrical focusing capabilities.

The lens controller may control a variety or lens system or optical system parameters, including any or all of transmissivity of the lens system over one or more spectral wavebands, intensity of light generated by an optical system, effective aperture of one or more components of the adjustable lens or optical system, transverse position of at least one optical element relative to the optical axis of the eye, or one or more chromatic aberration correcting features of the adjustable lens system.

Timing is an important consideration in the operation of many embodiments. In order to provide ongoing adaptive visual modification, correction or enhancement, the system updates the setting of the adjustable lens system in real-time or near-real-time. Moreover, in order to provide true adaptive vision correction, the focus of the adjustable lens system is adjusted to compensate for the current state of the eye optics and for the current visual input, without a priori knowledge of the visual input. In some cases this may be accomplished by completing a full update cycle (i.e., the flow process loop depicted in FIGS. 4, 5, 7, or 9) in an amount of time less than or equal to the intrinsic accommodation time of lens of eye. The intrinsic accommodation time of the lens of the eye (i.e., that amount of time that it takes for the lens to adjust to a change in the distance to a visual target) is from about 2 to about 3 seconds for a large change in focal distance, and varies from subject to subject. Accommodation rates and accommodation range vary as functions of age and health, being higher for children and lower for older adults. By adjusting the lens system faster than the intrinsic accommodation time, the lens-actuating musculature of the eye will be minimally worked, thus reducing eye strain and/or fatigue of eye muscles.

In some use-cases it may be desirable to update the setting of the adjustable lens system at a rate that is as fast, or faster, than the visual pigment reversal rate of photoreceptors of eye. In particular, in some embodiments, it may be desirable to update the lens setting at a rate faster than that of the photoreceptors having the fastest visual pigment reversal rate. In some embodiments, a controller is configured to provide closed loop control of the adjustable lens system on an ongoing basis. In some embodiments, the lens controller is configured to adjust the adjustable lens system at a rate faster than the intrinsic accommodation time of the lens of the eye. In other embodiments, the lens controller is configured to adjust the adjustable lens system at a rate faster than the visual pigment reversal rate of the photoreceptors of the eye.

It is thought that lens system adjustment update rates of at least about once every three seconds (1/3 Hz) may improve usefulness in general applications, and that update rates of about 1 Hz will be preferable for general applications. In higher-performance applications, update rates of about 3 Hz may be desirable. Update rates higher than 10 Hz may not provide additional benefit in some applications, due to the speed limitations inherent in other parts of the human visual system, though in some applications, this may not be the case. Thus, it is thought that update rates in the range of about 1/3 to about 10 Hz will be useful in practice, and that update rates in the range of about 1 to about 10 Hz will be more preferred, and that rates in the range of about 1 to about 3 Hz will be most preferred.

Timing of the update rate for lens system adjustment may be controlled in a number of ways. For example, each update cycle may be initialized by a signal from a timer chip or system clock; a software loop with an approximately fixed cycle time may also control the timing. The design of systems using these and other timing control methods are well known to those of skill in the art.

In some cases, in order to provide for rapid adjustment between one lens setting and at least one other lens setting, rather than utilizing a single adjustable lens system and modifying the setting of that lens system, two or more adjustable lenses, lens systems or optical systems may be used, and suitable optics used to switch between the two or more lenses, lens systems, or optical systems. In the exemplary case of two lens subsystems, one useful application of this embodiment is to adjust the first and second optical subsystems to provide correction for near and far vision, respectively. Thus, switching between the two optical subsystems, the subject would obtain correction similar to what is currently provided by bi-focal lenses, but in an automated fashion.

Figure 11:
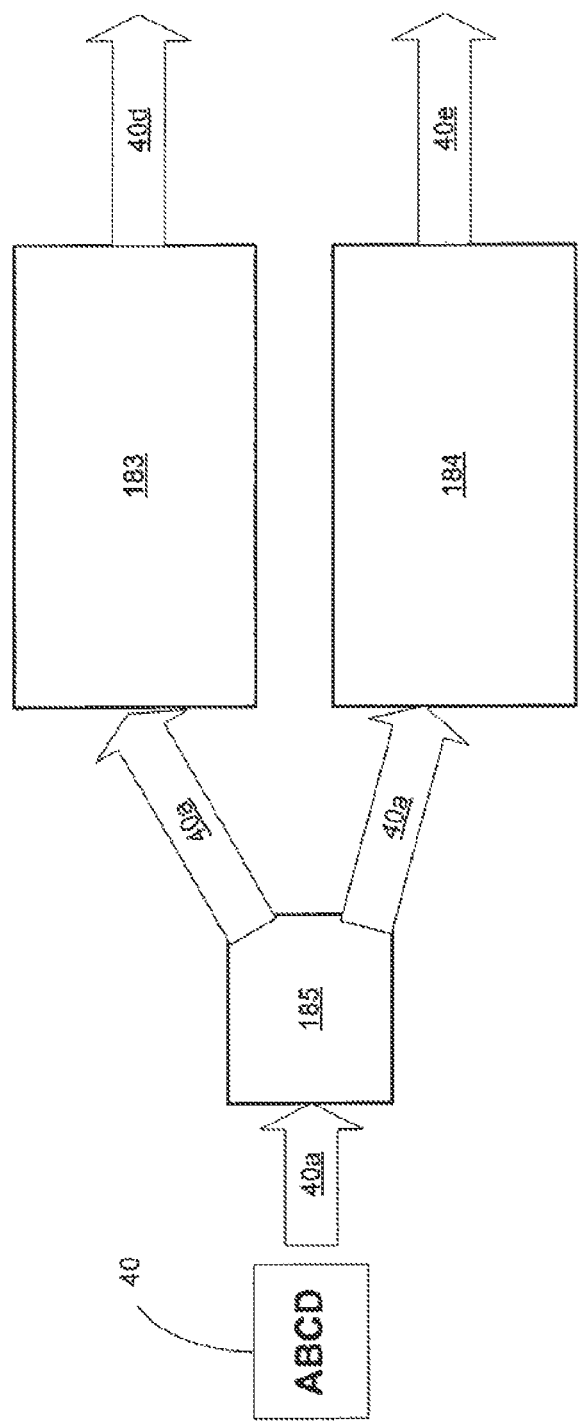
FIG. 11 illustrates an embodiment having two parallel optical paths.

This approach is depicted schematically in FIG. 11. First optical subsystem 183 and second optical subsystem 184 have optical properties (e.g. spherical focal length, cylindrical focal power, and axis of orientation) that can be adjusted independently. First optical subsystem 183 and second optical subsystem 184 are set up in parallel between a visual target 40 and the eye of the subject. Input image 40a may be switched rapidly between optical subsystem 183 and optical subsystem 184 by switching element 185, which may be an adjustable reflector, or refractive element, such as a lens. Each of optical subsystem 183 and optical subsystem 184 may be an adjustable lens or lens system, controlled by a lens controller as described previously. After passing through either optical subsystem 183 or optical subsystem 184, an intermediate incident image 40d or 40e, respectively, will be delivered to the eye of the subject. The optical system as depicted in FIG. 11 may be used in connection with image detection and lens control mechanisms as described previously herein.

Figure 12:
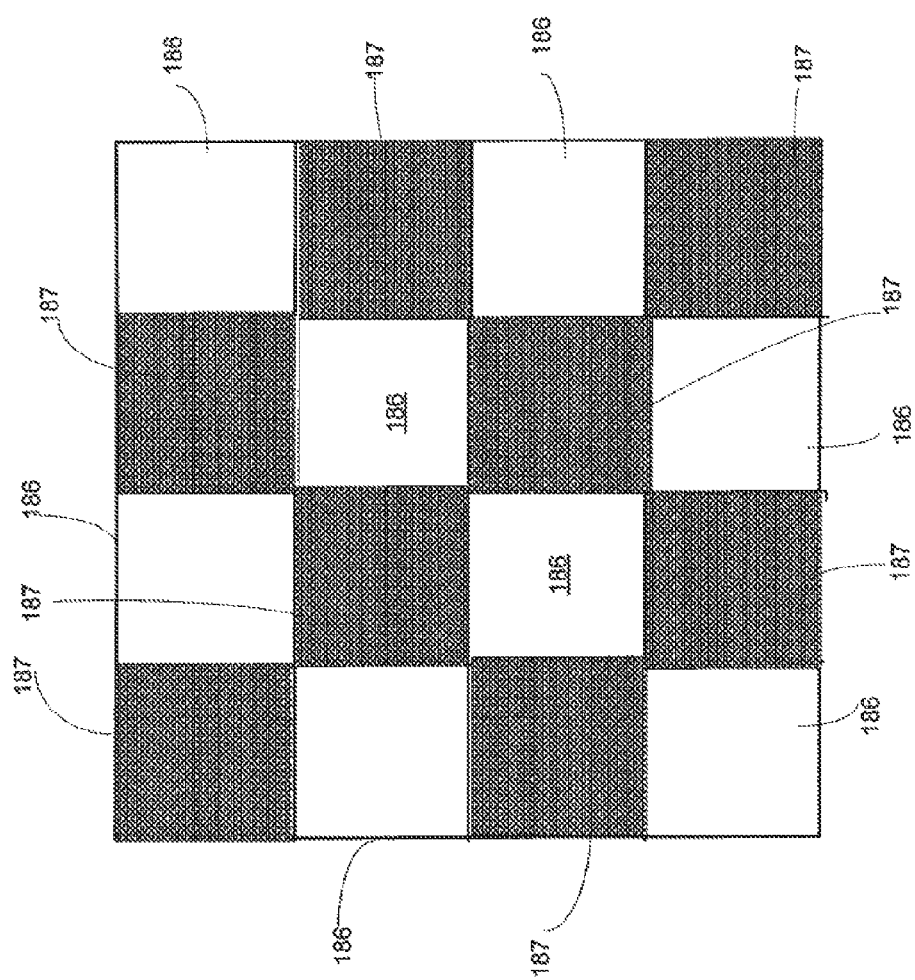
FIG. 12 illustrates the construction of an adjustable lens having two parallel optical subsystems.

Another method for providing rapid switching between optical subsystems having different settings is to provide two or more optical subsystems having transmissivities controllable between substantially complete transmissivity and substantially zero transmissivity, such that the amount of light that is transmitted through each subsystem can be controlled. Parallel subsystems are maintained in the optical path between the eye and the visual target; by adjusting the controllable transmissivities of respective parallel subsystems appropriately, it is possible to switch rapidly between multiple subsystems. Parallel optical subsystems of this type may be constructed in the form of an electroactive lens in which individually controllable lens areas are interleaved, as illustrated in FIG. 12, by microfabrication techniques known to those of skill in the relevant art. Thus, lens regions 186 correspond to a first optical subsystem, while lens regions 187 correspond to a second optical subsystem; adjustment of the transmissivities of lens regions 186 to provide substantially full transmissivity while adjusting the transmissivities of lens regions 187 to substantially zero transmissivity thus routes the visual input through the first optical subsystem. Conversely, adjustment of the transmissivities of lens regions 186 to provide substantially zero transmissivity while adjusting the transmissivities of lens regions 187 to substantially full transmissivity routes the visual input through the second optical subsystem. Different interleaving patterns can support three or more different optical subsystems.

Switching between first and second or more optical subsystems according to either of the above described methods could be controlled manually by the subject, by pushing a button or intentionally generating a readily detected control signal (a blink, etc.) or controlled automatically in response to vergence movement of eyes, change in distance to the visual target (detected, for example, by a rangefinder, which may be operable to provide an indication of a distance to a visual target so that the controller activates the switching mechanism responsive to the indication of distance to the visual target), or a sufficiently large change in focal quality of the detected image. According to either of the above embodiments, one or more of the optical subsystems may be adjusted to the current state of the visual input and the eye optics of the subject in order to compensate for gradual changes in focal quality, while switching between the subsystems may be used to compensate for more abrupt changes (for example, when the subject switches abruptly from a near vision task, such as reading the dashboard display of a car, to a distance vision task, such as looking at the road ahead).

Various components of the system, including the adjustable lens system, processor, and input and output image detectors may require some form of power supply. While the invention is not limited to any particular type of power supply, if the power supply is to be included in an eyeglass frame, contact lens, or intraocular lens device, it will typically be small and lightweight. For embodiments in which the adjustable lens system is mounted in an eyeglass frame, the device may be conveniently powered by a battery. Photovoltaic cells may also be used to provide power to the device. The power supply and possibly other components of the device as well may be located at a distance from the adjustable lens system, and power transmitted to the device, e.g. by inductive coupling or power-beaming. The power supply may include an inductive coil or antenna.

In some embodiments, the body of the subject may be used as a power source for powering the device. Various "energy scavenging" or "energy harvesting" devices are known, or may be developed (see e.g., U.S. Pat. Nos. 6,615,074, 6,655,035 and 6,768,246, and published U.S. Patent applications 20030014091 and 20030165648, all of which are incorporated herein by reference). For example, devices that capture energy from body movement of the subject (e.g., inertial devices as are used to power self-winding wristwatches) may be used to power the device. Pressure and chemical gradients within the body may also provide energy for powering operation of the device. For example, energy may be captured from the systolic-diastolic cycle or pulsatile blood flow of subject, through a microturbine or powered shunt placed in the respired airflow of the subject. Energy scavenging devices may scavenge energy from the environment, as well. Although reference has been made to a single power supply, the invention is not limited to use of a single power supply, and in some embodiments separate power supplies may be used for different part of the system, during different circumstances of operation, or both. Various components of the system may have different power sources, and the system as a whole may have one or multiple power sources of various types and is not limited to any specific power source configuration.

Figure 13:
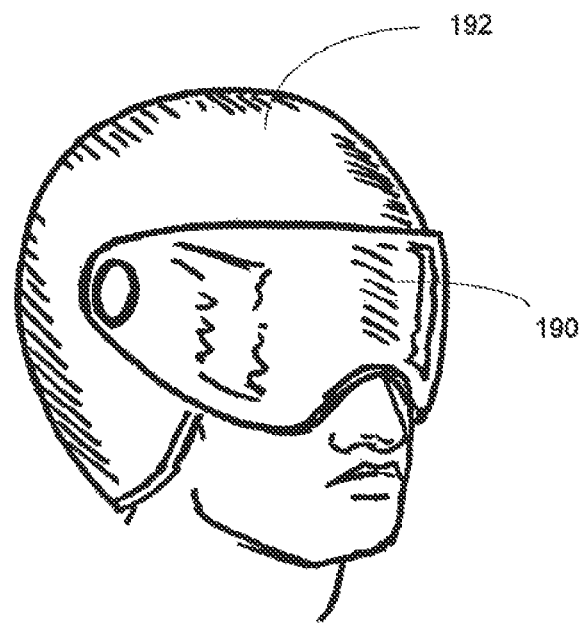
FIG. 13 shows a helmet-mounted implementation.
Figure 14:
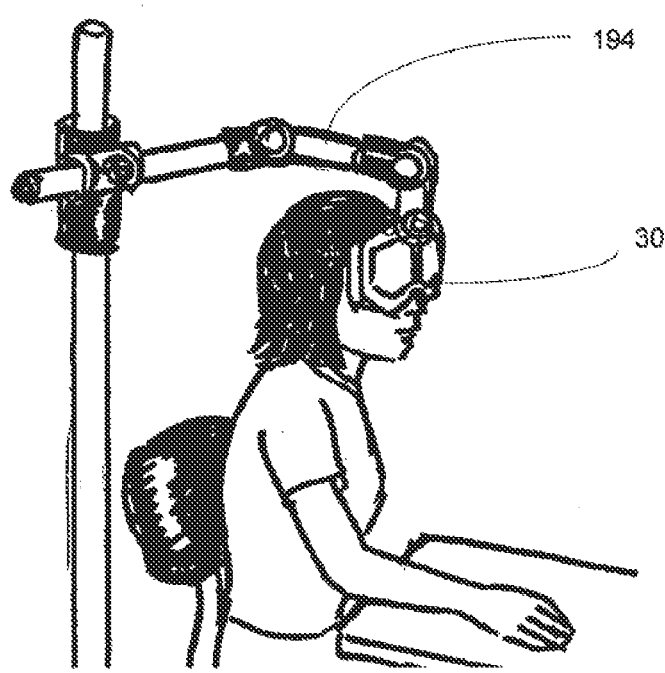
FIG. 14 shows implementation in an alternative mounting.

Adjustable lens system 26, output image detector 32, and input image detector 35 (if used) are positioned with respect to eye 10 of the subject 28 via mounting 30. Mounting 30 may take various forms, examples of which are illustrated in FIGS. 13 and 14. Mounting 30 may be an eyeglass frame, as depicted previously in FIG. 2, or helmet mounted frame 190, as in FIG. 13. Helmet 192 may be of the type worn by an airplane pilot, for example. Alternatively, mounting 30 may include a mechanical linkage 194 secured to a wall or ceiling or mounted on a base set on a table or floor, such that, in use, the subject stands or sits, and the equipment is held in fixed relationship to the subject's eye, but is not attached directly to the subject's head. As with the embodiments of the system in which mounting 30 is an eyeglass frame, other components of the system may be mounted on the mounting, or may be packaged separately.

The adjustable lens system may be implemented in the form of an eyeglass lens, a contact lens, or intraocular lens device. The adjustable lens system (or at least a portion thereof) may be formed in, on, or in spatial association with such lenses, including placement behind or in front of such lenses, in addition to being housed in or formed integrally with such lenses. It may also be implemented in other forms;

as depicted in FIGS. 13 and 14 it may be mounted in a helmet or in a stationary mount of the type used for optometric devices. The latter implementations are bulkier and present greater flexibility with regard to choice of system components and integration thereof. Although a helmet is depicted in FIG. 13, it will be appreciated that optical system components may be positioned with respect to the head by a variety of head mounted devices or structures, including headbands, hats, and other head coverings, which may not only provide support to system components but also function as head apparel or adornment. For implementation of the system as eyeglasses, and more particularly in the form of a contact lens or intraocular lens device, system components that are to be located in or on the lens (e.g., the lens actuator and image detector(s)) will preferably be very small, light weight and of modest time-averaged power demand. Certain components of the system may be packaged separately from the adjustable lens system, thereby reducing size and weight constraints. For example, certain components of the system can be packaged in a case that can be carried in, for example, the subject's pocket. Wireless transmission of data, control and power signals may be achieved via RF transmission or inductive coupling or beaming. Various portions of the system may also include transmission and receiving devices to provide for sending signals between physically separated system components. Digital signals are thought to be particularly suited for effectively error-free transmission in such embodiments, but the practice of the methods herein are not limited to any particular method of data transmission. For eyeglass, helmet, or stationary mount devices, wiring may be satisfactory for carrying power, data and control signals.

Figure 15:
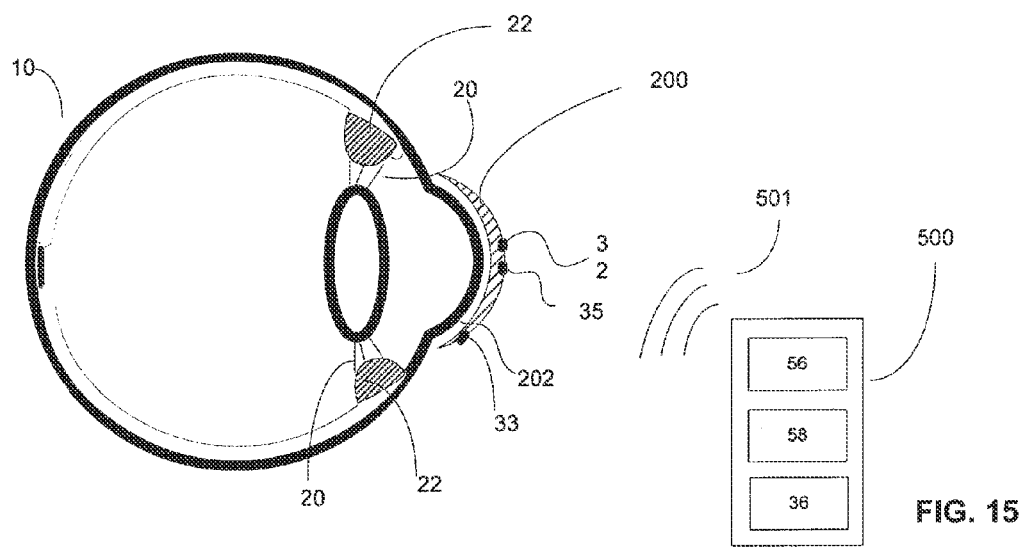
FIG. 15 illustrates an embodiment implemented in a contact lens.

In a further alternative embodiment, illustrated in FIG. 15, the adjustable lens system is constructed in the form of a contact lens 200 that is worn on the cornea 202 of eye 10. Output image detector 32, optional light source 33 (if used) and input image detector 35 may be attached to or manufactured integrally with the contact lens 200, so that they may be positioned appropriately with respect to the eye of the subject. Small size, low weight, and biocompatibility are important characteristics of components of this device. Other components of the system, including image analyzer 56, lens controller 58, and power supply 36 may be packaged separately in a remote device 500 at a remote location, and power and data signals 501 transmitted to the contact lens 200 inductively or via other suitable mechanisms, as depicted in FIG. 15; alternatively, additional components may be mounted on or manufactured integrally with contact lens 200. The term 'remote location', as used herein, refers to any location not in direct physical contact with contact lens 200, including positions relatively close to the contact lens on the body of the subject, more distant locations on the body of the subject, or locations separated from and at a distance from the body of the subject.

Figure 16:
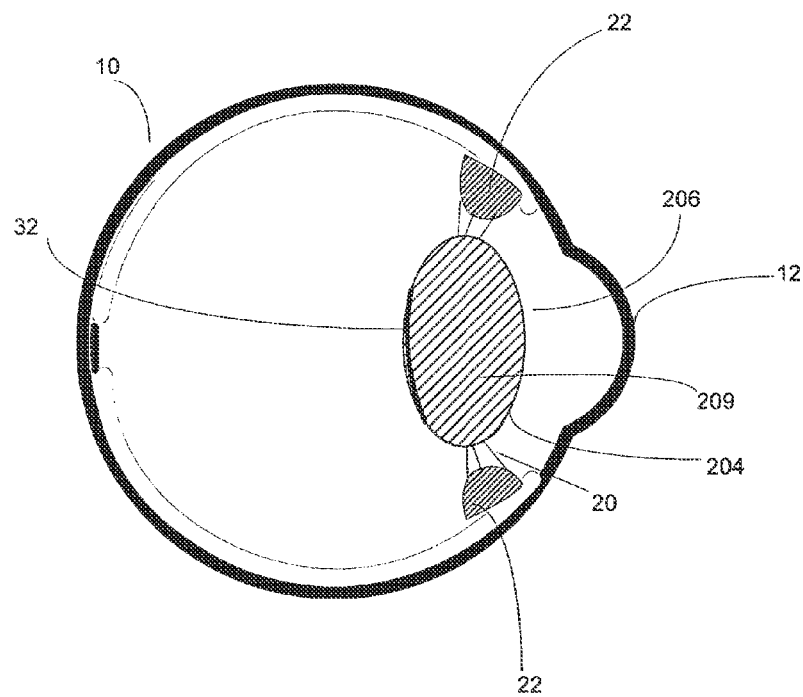
FIG. 16 illustrates an embodiment implemented as an intraocular lens device.

Some embodiments of the systems and devices described herein may also be configured as an intraocular lens device 206, as depicted in FIG. 16. Intraocular lens device 206 includes lens system 209 and output image detector 32. Other components of the system, including image analyzer 56, lens controller 58, and power supply 36 may be packaged separately in a remote device (not shown) of the type used in the embodiment of FIG. 15. An optional light source may be mounted in intraocular lens device 206 (not shown in FIG. 16). For the embodiment of FIG. 16, the functional flow diagram will be as illustrated in schematic form in FIG. 17. Input image 40*a* passes through eye optics 208, through adjustable lens system 209 and to retina 16. Intraocular lens device 206 may also include output image detector 32. In an intact eye, the eye optics include the cornea and lens. In the implementation of the system or device as an intraocular lens device, it is anticipated that the natural lens will have been removed and the adjustable intraocular lens device implanted within the eye. Various adjustable intraocular lens designs may be used in this embodiment, as exemplified by U.S. Pat. Nos. 4,373,218, 4,564,267, 4,601,545, 4,787,903, and 5,108,429, all of which are incorporated herein by reference in their entirety. The eye optics will then include the cornea. However, in some cases the intraocular lens device may be implanted either in front of or behind the natural lens, so that the eye optics may include the natural lens as well as the cornea. The intraocular version is not restricted to use with any particular combination of eye optics, though the correction provided by the lens system optics will typically take into account the degree of focus provided by the eye optics.

Figure 17:
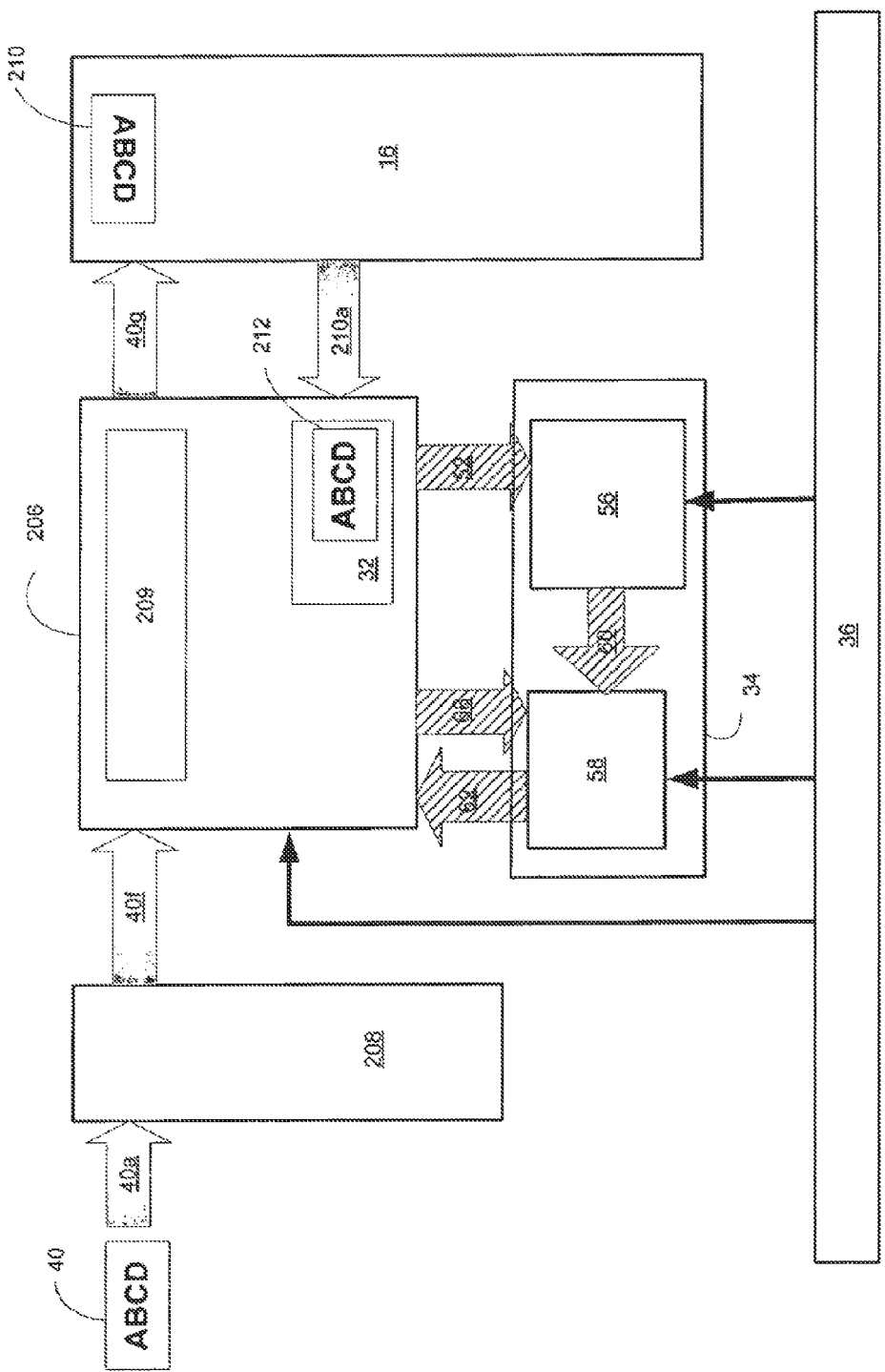
FIG. 17 is a schematic diagram of the embodiment shown in FIG. 16.

Referring back to FIG. 17, retinal image 210 is reflected from retina 16 as intermediate reflected image 210*a*, and arrives at output image detector 32 as reflected image 212. Output image detector 32 creates a representation of reflected image 212 as a digital output image signal 52 which is transmitted to image analyzer 56. Output image signal 52 is processed by image analyzer 56 to determine whether and how lens system 209 should be adjusted to improve the quality of the retinal image. Sharpness signal 60 is generated by image analyzer 56 and sent to lens controller 58. Lens controller 58 generates lens control signal 62. Lens controller 58 may also receive as input a lens state signal 68 that provides information regarding the current state of adjustable lens 206. Adjustable lens system 209, lens controller 58, output image detector 32, and image analyzer 56 are powered by power supply 36. As in the previous embodiment, adjustable lens system 209, and output image detector 32, are attached to or manufactured integrally with intraocular lens device 206. Size, weight, and biocompatibility requirements may be stringent for these components of the system. Other components of the system, including image analyzer 56, lens controller 58, and power supply 36 may be packaged separately at a remote location and power and data signals transmitted to intraocular device 206, or in some cases they may be mounted on or manufactured integrally with intraocular device 206. As noted previously, the term 'remote location', as used herein, refers to any location not in direct physical contact with the intraocular lens device, and may include positions relatively close to the contact lens in or on the body of the subject, as well as more distant locations not on the body of the subject. Operation of the device configured as an intraocular lens device, as illustrated in FIG. 17, is substantially the same as that of other, previously described embodiments, for example, as illustrated in the flow diagram of FIG. 4 or 5.

With regard to the hardware and/or software used in image detection and analysis, as well as various aspects of device control, those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency or implementation convenience tradeoffs. Those having skill in the art will appreciate that there are various vehicles by which processes and/or systems described herein can be effected (e.g., hardware, software, and/or firmware), and that the preferred vehicle will vary with the context in which the processes are deployed. For example, if an implementer determines that speed and accuracy are paramount, the implementer may opt for a hardware and/or firmware vehicle; alternatively, if flexibility is paramount, the implementer may opt for a solely software implementation; or, yet again alternatively, the implementer may opt for some combination of hardware, software, and/or firmware. Hence, there are several possible vehicles by which the processes described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will require optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be implicitly understood by those with skill in the art that each function and/or operation within such block diagrams, flowcharts, or examples can be implemented, individually and/or collectively, by a wide range of hardware, software, firmware, or virtually any combination thereof. In one embodiment, several portions of the subject matter subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in standard integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the capabilities of one of skill in the art in light of this disclosure. In addition, those skilled in the art will appreciate that certain mechanisms of the subject matter described herein are capable of being distributed as a program product in a variety of forms, and that an illustrative embodiment of the subject matter described herein applies equally regardless of the particular type of signal bearing media used to actually carry out the distribution. Examples of a signal bearing media include, but are not limited to, the following: recordable type media such as floppy disks, hard disk drives, CD ROMs, digital tape, and computer memory; and transmission type media such as digital and analog communication links using TDM or IP based communication links (e.g., links carrying packetized data).

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment).

Those skilled in the art will recognize that it is common within the art to describe devices for image detection and analysis, optical system control, and/or processes in the fashion set forth herein, and thereafter use standard engineering practices to integrate such described devices and/or processes into vision enhancement systems as exemplified herein. That is, at least a portion of the devices and/or processes described herein can be integrated into a vision enhancement system via a reasonable amount of experimentation. Those having skill in the art will recognize that such systems generally include one or more of a memory such as volatile and non-volatile memory, processors such as microprocessors and digital signal processors, computational-supporting or—associated entities such as operating systems, user interfaces, drivers, sensors, actuators, applications programs, one or more interaction devices, such as data ports, control systems including feedback loops and control implementing actuators (e.g., devices for sensing position and/or velocity and/or acceleration or time-rate-of-change thereof; control motors for moving and/or adjusting components and/or quantities). A typical vision enhancement system may be implemented utilizing any suitable available components, such as those typically found in appropriate computing/communication systems, combined with standard engineering practices.

The foregoing-described aspects depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermediate components. Likewise, any two components so associated can also be viewed as being "operably connected", or "operably coupled", to each other to achieve the desired functionality.

While particular aspects of the present subject matter described herein have been shown and described, it will be obvious to those skilled in the art that, based upon the teachings herein, changes and modifications may be made without departing from this subject matter described herein and its broader aspects and, therefore, the appended claims are to encompass within their scope all such changes and modifications as are within the true spirit and scope of this subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should NOT be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" and/or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense of one having skill in the art would understand the convention (e.g., "a system having at least one of A, B, and C" would include but not be limited to systems that have A alone, B alone, C alone, A and B together, A and C together, B and C together, and/or A, B, and C together). In those instances where a convention analogous to "at least one of A, B, or C, etc." is used, in general such a construction is intended in the sense of one having skill in the art would understand the convention (e.g., "a system having at least one of A, B, or C" would include but not be limited to systems that have A alone, B alone, C alone, A and B together, A and C together, B and C together, and/or A, B, and C together).

Although the methods, devices, systems and approaches herein have been described with reference to certain preferred embodiments, other embodiments are possible. As illustrated by the foregoing examples, various choices of adjustable lens system configuration and image detector configuration may be within the scope of the invention. As has been discussed, the choice of system configuration may depend on the intended application of the system, the environment in which the system is used, cost, personal preference or other factors. Image analysis and lens control processes may be modified to take into account choices of lens system and image detector configuration, and such modifications, as known to those of skill in the arts of image analysis, control system design, and other relevant arts, may fall within the scope of the invention. Therefore, the full spirit or scope of the invention is defined by the appended claims and is not be limited to the specific embodiments described herein.

The invention claimed is:

1. An adaptive vision modification system, comprising:
   at least one sensor for detecting a neuromuscular signal from a ciliary muscle of a subject;
   an adjustable intraocular lens including an adjustable optical element for modifying a visual input to the subject;
   a processor operatively connected to the at least one sensor and the adjustable intraocular lens, the processor including
      a signal input for receiving the neuromuscular signal from the at least one sensor;
      a pre-processor for performing preliminary signal processing of the neuromuscular signal to produce a pre-processed signal;
      a signal analyzer configured to analyze the pre-processed signal to generate as output at least one quality parameter characterizing a quality of the visual input at a retina of the subject; and
      a lens system controller configured to receive as input the at least one quality parameter and to generate as output a control signal for controlling the adjustable intraocular lens in response to the at least one quality parameter; and
   a remote portion including
      at least a portion of one or more of the pre-processor, the signal analyzer, and the lens system controller;
      a transmitter for transmitting at least one of a data signal and a control signal to at least one of the adjustable intraocular lens and the at least one sensor; and
      a receiver for receiving at least one of a data signal and a control signal from at least one of the adjustable intraocular lens and the at least one sensor.

2. The adaptive vision modification system of claim 1, wherein at least a portion of the adaptive vision modification system is implemented as a computing system including at least one of a volatile semiconductor-based memory, a nonvolatile semiconductor-based memory, a user interface and a data port.

3. The adaptive vision modification system of claim 1, wherein at least a portion of the adaptive vision modification system is implemented utilizing components of a communication system.

4. The adaptive vision modification system of claim 1, wherein at least a portion of the adaptive vision modification system is implemented utilizing components of a computing system.

5. The adaptive vision modification system of claim 1, including a power supply.

6. The adaptive vision modification system of claim 5, wherein the power supply is a battery.

7. The adaptive vision modification system of claim 5, including a transmitter for transmitting power from the power supply to at least one of the adjustable intraocular lens and the at least one sensor via power beaming.

8. The adaptive vision modification system of claim 5, including an inductive coil for delivering power from the power supply to at least one of the adjustable intraocular lens and the at least one sensor via inductive coupling.

9. The adaptive vision modification system of claim 1, wherein the adjustable optical component includes an electroactive component.

10. The adaptive vision modification system of claim 1, wherein the adjustable optical component includes a liquid crystal component.

11. The adaptive vision modification system of claim 1, wherein the adjustable optical component includes a polymeric component.

12. The adaptive vision modification system of claim 1, wherein the transmitter is adapted to transmit the at least one of a data signal and a control signal to the at least one of the adjustable intraocular lens and the at least one sensor as a radio frequency signal.

13. The adaptive vision modification system of claim 1, wherein the transmitter is adapted to transmit the at least one of a data signal and a control signal to the at least one of the adjustable intraocular lens and the at least one sensor via an inductive coupling.

14. The adaptive vision modification system of claim 1, wherein the receiver is adapted to receive the at least one of a data signal and a control signal from the at least one of the adjustable intraocular lens and the at least one sensor as a radio frequency signal.

15. The adaptive vision modification system of claim 1, wherein the receiver is adapted to receive the at least one of a data signal and a control signal from the at least one of the adjustable intraocular lens and the at least one sensor via an inductive coupling.

16. The adaptive vision modification system of claim 1, wherein the at least one sensor includes an electrode.

17. The adaptive vision modification system of claim 1, wherein the at least one sensor includes an optoelectronic sensor.

18. The adaptive vision modification system of claim 1, wherein the at least one sensor is adapted to detect an electromagnetic signal.

19. The adaptive vision modification system of claim 1, wherein the at least one sensor includes an electromyographic signal.

20. The adaptive vision modification system of claim 1, wherein the lens system controller is configured to provide closed loop control of the adjustable intraocular lens on an ongoing basis.

21. The adaptive vision modification system of claim 1, wherein the lens system controller is configured to generate the control signal based upon a pre-determined relationship between the at least one quality parameter and the visual input.

22. The adaptive vision modification system of claim 1, wherein the lens system controller is configured to accept a magnification factor input.

23. The adaptive vision modification system of claim 22, wherein said lens system controller is adapted to adjust the adjustable intraocular lens in response to the magnification factor and the quality parameter.

24. An intraocular lens controller, comprising:
   a receiver for receiving a visual focal condition signal indicative of a visual focal condition from an adjustable intraocular lens system, the adjustable intraocular lens system including an adjustable intraocular lens including an adjustable optical element for modifying a visual input to the subject, at least one sensor for detecting a neuromuscular signal indicative of the visual focal condition from a ciliary muscle of a subject, and a transmitter for transmitting a visual focal condition signal based in the detected neuromuscular signal;
   a signal analyzer configured to analyze the visual focal condition signal to generate as output at least one quality parameter characterizing a quality of the visual input at a retina of the subject; and
   a lens system controller configured to receive as input the at least one quality parameter and to generate as output a control signal for controlling the adjustable intraocular lens in response to the at least one quality parameter; and
   a transmitter for transmitting the control signal to the adjustable intraocular lens system.

25. The adaptive vision modification system of claim 24, wherein the transmitter is adapted to transmit a radio frequency signal.

26. The adaptive vision modification system of claim 24, wherein the transmitter is adapted to transmit the control signal via an inductive coupling.

27. The adaptive vision modification system of claim 24, wherein the receiver is adapted to receive the visual focal condition signal as a radio frequency signal.

28. The adaptive vision modification system of claim 24, wherein the receiver is adapted to receive the visual focal condition signal via an inductive coupling.

29. The intraocular lens controller of claim 24, including a power supply; and
   a transmitter for transmitting power from the power supply to at least one of the adjustable intraocular lens and the at least one sensor via power beaming.

30. The intraocular lens controller of claim 24, including a power supply; and
   an inductive coil for delivering power from the power supply to at least one of the adjustable intraocular lens and the at least one sensor via inductive coupling.

31. The intraocular lens controller of claim 24, wherein at least a portion of the intraocular lens controller is implemented utilizing components of a communication system.

32. The intraocular lens controller of claim 24, wherein at least a portion of the intraocular lens controller is implemented utilizing components of a computing system.

33. The intraocular lens controller of claim 24, wherein the lens system controller is configured to provide closed loop control of the adjustable intraocular lens on an ongoing basis.

34. The intraocular lens controller of claim 24, wherein the lens system controller is configured to generate the control signal based upon a pre-determined relationship between the at least one quality parameter and the visual input.

35. The intraocular lens controller of claim 24, wherein the lens system controller is configured to accept a magnification factor input.

36. The intraocular lens controller of claim 35, wherein said lens system controller is adapted to generate the control signal in response to the magnification factor and the quality parameter.

37. A method of controlling an adaptive intraocular lens, comprising:
   detecting, with at least one sensor, a neuromuscular signal from a ciliary muscle of a subject, the neuromuscular signal indicative of a quality of a visual input at a retina of the subject;
   receiving the neuromuscular signal, via a signal input, at a processor operatively connected to the at least one sensor, the processor including the signal input for receiving the neuromuscular signal from the at least one sensor, a pre-processor for performing preliminary signal processing of the neuromuscular signal, a signal analyzer, and a lens system controller;
   performing preliminary signal processing of the neuromuscular signal with the pre-processor to produce a pre-processed signal;
   analyzing the pre-processed signal with the signal analyzer to generate as output at least one quality parameter characterizing the quality of the visual input at the retina of the subject;
   generating with the lens system controller, in response to the at least one quality parameter, a control signal for controlling the adjustable intraocular lens; and
   transmitting the control signal from the processor to the adjustable intraocular lens with the transmitter.

38. The method of claim 37, including receiving the neuromuscular signal at the signal input via an RF coupling.

39. The method of claim 37, including receiving the neuromuscular signal at the signal input via an inductive coupling.

40. The method of claim 37, including receiving the neuromuscular signal at the signal input via by transponder-type sensor.

41. The method of claim 37, including
- accepting, via a user interface operatively connected to the processor, a magnification factor input; and
- generating the control signal with the lens system controller in response to the magnification factor and the at least one quality parameter.

42. The method of claim 37, including transmitting power, from a power supply operatively connected to the processor, to the adjustable intraocular lens via power beaming.

43. The method of claim 37, including transmitting power, from a power supply operatively connected to the processor, to the adjustable intraocular lens via inductive coupling.

* * * * *